(12) United States Patent
Gabizon et al.

(10) Patent No.: US 10,617,672 B2
(45) Date of Patent: Apr. 14, 2020

(54) LIPOSOME COMPOSITION CO-ENCAPSULATING DOXORUBICIN AND A PRODRUG OF MITOMYCIN C

(71) Applicants: LIPOMEDIX PHARMACEUTICALS LTD., Jerusalem (IL); SHAARE ZEDEK SCIENTIFIC LTD., Jerusalem (IL)

(72) Inventors: Alberto Gabizon, Jerusalem (IL); Patricia Ohana, Jerusalem (IL); Hilary Shmeeda, Givat Zev (IL)

(73) Assignees: Lipomedix Pharmaceuticals Ltd., Jerusalem (IL); Shaare Zedek Scientific Ltd., Jerusalem (IL)

( * ) Notice: Subject to any disclaimer, the term of this patent is extended or adjusted under 35 U.S.C. 154(b) by 0 days.

(21) Appl. No.: 15/768,526

(22) PCT Filed: Oct. 14, 2016

(86) PCT No.: PCT/US2016/057176
§ 371 (c)(1),
(2) Date: Apr. 13, 2018

(87) PCT Pub. No.: WO2017/066667
PCT Pub. Date: Apr. 20, 2017

(65) Prior Publication Data
US 2018/0296529 A1 Oct. 18, 2018

Related U.S. Application Data

(60) Provisional application No. 62/242,097, filed on Oct. 15, 2015.

(51) Int. Cl.
*A61K 9/127* (2006.01)
*A61K 31/407* (2006.01)
(Continued)

(52) U.S. Cl.
CPC .......... *A61K 31/407* (2013.01); *A61K 9/0019* (2013.01); *A61K 9/127* (2013.01);
(Continued)

(58) Field of Classification Search
CPC .. A61K 9/127; A61K 31/407; A61K 47/6911; A61K 47/544; A61K 9/0019; A61K 31/704; A61P 35/04
See application file for complete search history.

(56) References Cited

U.S. PATENT DOCUMENTS

| | | |
|---|---|---|
| 5,192,549 A | 3/1993 | Barenolz et al. |
| 2010/0247629 A1 | 9/2010 | Gabizon et al. |

(Continued)

FOREIGN PATENT DOCUMENTS

| | | |
|---|---|---|
| WO | 2013/008240 | * 1/2013 |
| WO | WO 2015/191563 A1 | 12/2015 |
| WO | WO 2017/066667 A1 | 4/2017 |

OTHER PUBLICATIONS

Trosko, J.e., et al in Mutation Research, 480-481, pp. 219-229, 2001.*

(Continued)

*Primary Examiner* — Gollamudi S Kishore
(74) *Attorney, Agent, or Firm* — McDermott Will & Emery LLP; Judy M. Mohr; Wen Li

(57) ABSTRACT

A composition comprising liposomes comprising a lipid layer defining an internal aqueous compartment, an anthracycline drug entrapped in the internal aqueous phase and mitomycin C prodrug incorporated into the lipid layer is described.

13 Claims, 27 Drawing Sheets

(51) Int. Cl.
*A61K 31/704* (2006.01)
*A61K 9/00* (2006.01)
*A61K 47/54* (2017.01)
*A61K 47/69* (2017.01)
*A61P 35/04* (2006.01)

(52) U.S. Cl.
CPC .......... *A61K 31/704* (2013.01); *A61K 47/544* (2017.08); *A61K 47/6911* (2017.08); *A61P 35/04* (2018.01)

(56) References Cited

U.S. PATENT DOCUMENTS

| | | |
|---|---|---|
| 2013/0052259 A1 | 2/2013 | Barenholz et al. |
| 2014/0212479 A1* | 7/2014 | Zeinelden ............ A61K 9/127 424/450 |
| 2014/0328899 A1 | 11/2014 | Gabizon et al. |
| 2014/0328905 A1* | 11/2014 | Fologea ............ A61K 9/0009 424/450 |

OTHER PUBLICATIONS

Cheung et al., "In vivo efficacy and toxicity of intratumorally delivered mitomycin C and its combination with doxorubicin using microsphere formulations", Anti-Cancer Drugs, vol. 16, pp. 423-433 (2005).

Gabizon et al., "Reduced toxicity and superior therapeutic activity of a mitomycin C lipid-based prodrug incorporated in pegylated liposomes", Clin. Cancer Res. vol. 12, No. 6, pp. 1913-1920 (2006).

International Search Report and Written Opinion from International Patent Application No. PCT/US2016/057176, 13 pages, dated Jan. 16, 2017, application now published as International Publication No. WO2017/066667 dated Apr. 20, 2017.

Prasad et al., "Doxorubicin and mitomycin C co-loaded polymer-lipid hybrid nanoparticles inhibit growth of sensitive and multidrug resistant human mammary tumor xenografts", Cancer Letters, vol. 334, pp. 263-273 (2013).

Shuhendler et al., "A novel doxorubicin-mitomycin C co-encapsulated nanoparticle formulation exhibits anti-cancer synergy in multidrug resistant human breast cancer cells", Breast Cancer Res. Treat, vol. 119, pp. 255-269 (2010).

Shuhendler et al., "Synergistic nanoparticulate drug combination overcomes multidrug resistance, increases efficacy, and reduces cardiotoxicity in a nonimmunocompromised breast tumor models", Molecular Pharmaceutics, vol. 11, No. 8, pp. 2659-2674 (2014).

* cited by examiner

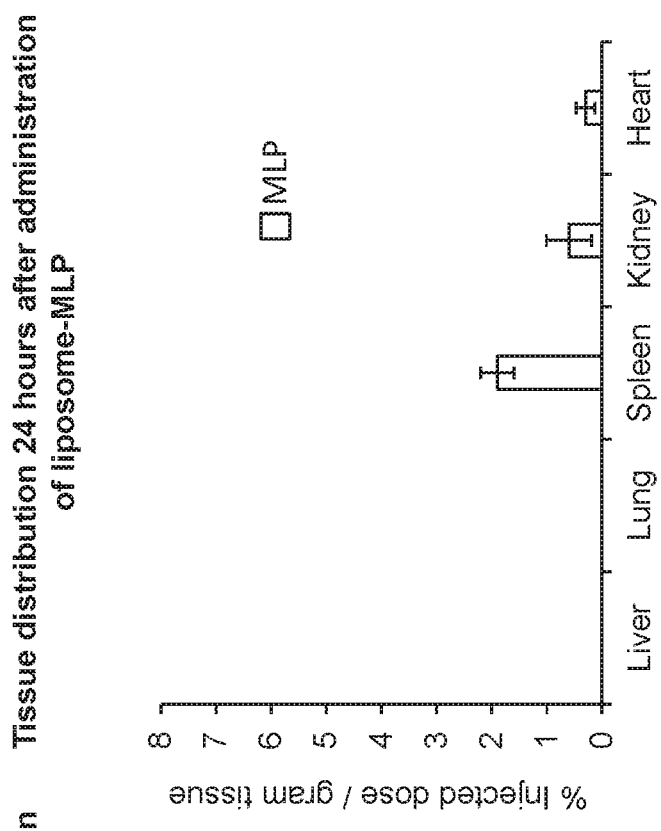
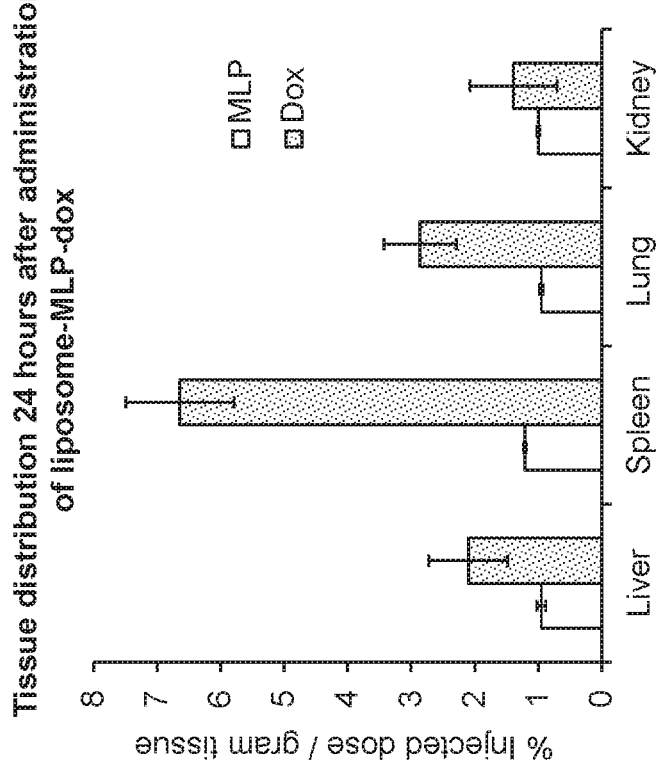
FIG. 14A
FIG. 14B

LIPOSOME COMPOSITION CO-ENCAPSULATING DOXORUBICIN AND A PRODRUG OF MITOMYCIN C

CROSS-REFERENCE TO RELATED APPLICATIONS

This application is a U.S. National Stage Application under 35 U.S.C. § 371 of International Patent Application No. PCT/US2016/057176, filed Oct. 14, 2016, which claims the benefit of U.S. Provisional Application No. 62/242,097, filed Oct. 15, 2015, each of which is hereby incorporated by reference in its entirety.

TECHNICAL FIELD

The subject matter described herein relates to liposomes with co-encapsulated doxorubicin and mitomycin C prodrug.

BACKGROUND

Cancer is a leading cause of death in the United States and affects people worldwide. Surgery, radiation therapy and chemotherapy are the most widely used therapeutic modalities. Development of new compositions and treatment regimens for cancer therapy that provide synergistic effects and minimal toxicity to the subject being treated would be advantageous.

BRIEF SUMMARY

The following aspects and embodiments thereof described and illustrated below are meant to be exemplary and illustrative, not limiting in scope.

In one aspect, a composition comprised of liposomes comprising a lipid layer defining an internal aqueous compartment, an anthracycline drug entrapped in the internal aqueous phase, mitomycin C prodrug incorporated into the lipid layer, and a pharmaceutically acceptable carrier is provided. In one embodiment, the composition is formulated such that upon administration an amount of the prodrug of mitomycin C yields a therapeutically-effective amount of mitomycin C in vivo.

In one embodiment, the prodrug is a conjugate of mitomycin C releasably attached to a lipophilic moiety. In one embodiment, the lipophilic moiety is a phospholipid.

In another embodiment, the lipid layer is a lipid bilayer.

In still another embodiment, the anthracycline drug is selected from doxorubicin, daunorubicin, epirubicin and idarubicin.

In yet another embodiment, the composition further comprises an ammonium salt. In one embodiment, the ammonium salt is an ammonium salt of a bisphosphonate. Exemplary bisphosphonates include alendronate, pamidronate, neridonate, olpadronate, ibandronate, risedronate and zoledronate. In another embodiment, the ammonium salt is an ammonium salt of sulfate, phosphate, glucuronide, sucralfate or dextran-sulfate.

In one embodiment, the prodrug is a conjugate of mitomycin C releasably attached to a lipophilic moiety and the anthracycline drug is doxorubicin.

In another aspect, a method for treating a neoplasm in a patient is provided. The method comprises providing a composition as described herein, and administering or instructing to administer the composition.

In one embodiment, administering or instructing to administer comprises administering or instructing to administer via injecting.

In another embodiment, injecting by intravenous, intraarterial, intraperitoneal, intrapleural, intrathecal, intravesical or intratumoral injection.

In yet another embodiment, providing comprises providing an amount of the composition to yield a therapeutically-effective amount of mitomycin C in vivo.

In other embodiments, the neoplasm in the patient is brain cancer, head and neck cancer, lung cancer, breast cancer, ovarian cancer, esophageal cancer, stomach cancer, pancreatic cancer, colorectal cancer, or bladder cancer.

In another aspect, a method for treating a solid tumor is provided. The method comprises providing a composition as described herein, and administering or instructing to administer the composition. In one embodiment, any tumor that is not a cancer of the blood is contemplated.

In one embodiment, the composition is not a polymer-lipid hybrid nanoparticle comprising doxorubicin and mitomycin-C.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

BRIEF DESCRIPTION OF THE DRAWINGS

FIG. 14A is a bar graph showing the percent of injected dose per gram of tissue of mitomycin C prodrug conjugate (open bars) and of doxorubicin (dotted bars) in mice liver, spleen, lung, and kidney 24 hours after injection of liposomes with co-encapsulated doxorubicin and mitomycin C prodrug (liposome-MLP-dox);

FIG. 14B is a bar graph showing the percent of injected dose per gram of tissue of mitomycin C prodrug conjugate (open bars) in mice liver, spleen, lung, kidney and heart 24 hours after injection of liposomes with mitomycin C prodrug conjugate (liposome-MLP)

DETAILED DESCRIPTION

I. Definitions

Figure 1A:
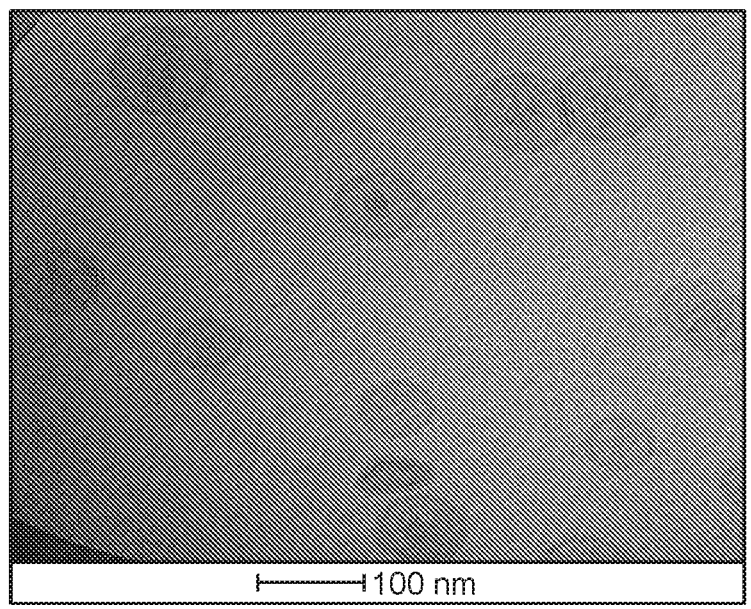
FIGS. 1A-1D are electron cryomicroscopy photographs of liposomes with co-encapsulated doxorubicin and mitomycin C prodrug prepared according to one embodiment.
Figure 1B:
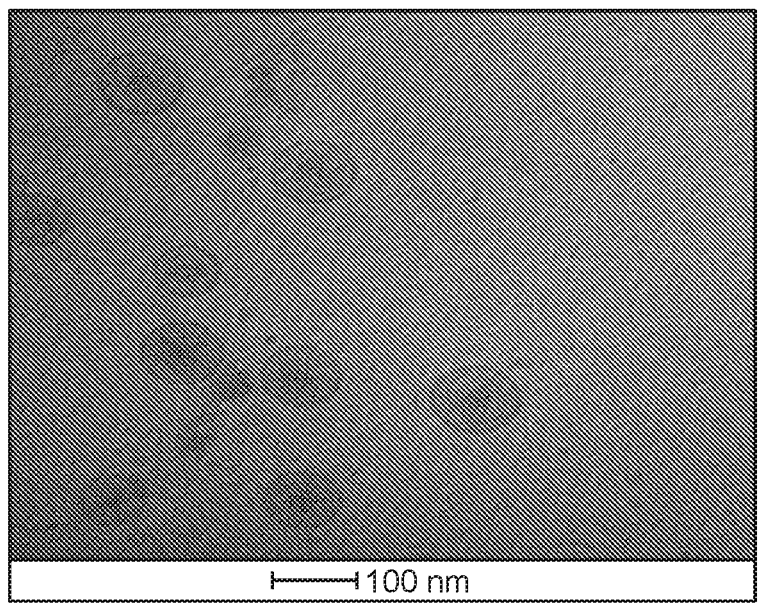

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

"Administering" or "administration" as used herein means the introduction of a foreign molecule into a cell or host. The term is intended to be synonymous with the term "delivery" or "delivering". Suitable routes of administration, without limitation, are intravenous, intra-arterial, intramuscular, subcutaneous, intraperitoneal, intrapleural, intrathecal, intravesical or intratumoral, intrasynovial, infusion, sublingual, transdermal, oral, or topical.

As used herein, the phrase "chemotherapeutic agent" is synonymous with and "antineoplastic agent" or "antiproliferative agent" and refers to compounds that prevent cancer, or hyperproliferative cells, from multiplying. Generally, antineoplastic agents may prevent cancer cells from multiplying by: (1) interfering with the cell's ability to replicate DNA and (2) inducing cell death and/or apoptosis in the cancer cells.

An amount of liposomal-mitomycin C prodrug that yields a therapeutically-effective amount of mitomycin C after administration is an amount of mitomycin C that is effective to ameliorate or minimize the clinical impairment or symptoms of the neoplasia, in either a single dose or in multiple doses.

As used herein, a "neoplasm" or "neoplasia" means a proliferative disease characterized by the abnormal proliferation of cells. Typically, neoplasia is associated with cancer and tumor formation. As used herein a "solid tumor" is one that occurs in an organ, such as the breast or the colon.

The term "patient" refers to an individual afflicted with a disease characterized by neoplasia. In particular, a patient (i.e., a host) is an animal (i.e., mammal) or human.

As used herein, "pharmaceutical formulations" include formulations for human and veterinary use with no significant adverse effect. "Pharmaceutically acceptable carrier" as used herein refers to a composition or formulation that allows for the effective distribution of the agents of the instant invention in the physical location most suitable for their desired activity and "pharmaceutically acceptable carrier" refers to a buffer, stabilizer or other material well known to those skilled in the art. Such materials should be non-toxic and should not interfere with the efficacy of the active ingredient. The precise nature of the carrier or other material may depend on the route of administration.

As used herein, "prodrug" means a compound that is a drug precursor which, following administration to a subject, releases the drug in vivo via some chemical or physiological process such that the prodrug is converted into a product that is toxic to cells of a neoplasm.

As used herein "synergistic effect" or "therapeutic synergy" refers to a clinical observation wherein a combination of mitomycin C and doxorubicin administered to a subject via injection of liposomes with co-encapsulated doxorubicin and mitomycin C prodrug provides more than additive effect of mitomycin C administered via a liposomal-mitomycin C prodrug alone and doxorubicin administered via liposome entrapped doxorubicin.

Reference to a "therapeutically effective amount," intends an amount of a compound sufficient to show benefit to the individual. This amount prevents, alleviates, abates, or otherwise reduces the severity of a symptom associated with neoplasia in a patient, such as a reduction in tumor mass or volume or a slowing of tumor growth rate.

The terms "treat," "treatment" and "therapeutic effect" as used herein refer to reducing or stopping a cell proliferation rate (e.g., slowing or halting tumor growth) or reducing the number of proliferating cancer cells.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms "a," "an," and "the" include plural referents unless the context clearly dictates otherwise. Thus, for example, reference to a "liposome" includes a single liposome as well as two or more of the same or different liposomes, reference to an "excipient" includes a single excipient as well as two or more of the same or different excipients, and the like.

II. Liposomes Co-Encapsulating an Anthracycline and a Mitomycin C Prodrug

In one aspect, a composition comprising liposomes that co-encapsulate doxorubicin and mitomycin C prodrug are provided. The components of the liposome composition will now be described.

The liposomal prodrug conjugate of mitomycin C provided for use in the methods described herein is, in one embodiment, comprised of mitomycin C releasably attached to a lipophilic or hydrophobic moiety, and generally is of the form:

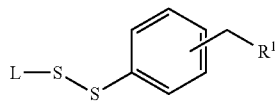

wherein L is a hydrophobic moiety, $R^1$ represents a mitomycin C residue covalently attached to the dithiobenzyl moiety. Orientation of the $CH_2R^1$ group is selected from the ortho position and the para position. Synthesis of the conjugate is described in U.S. Pat. Nos. 6,365,179; 6,984,396; and 7,303,760, each of which is incorporated by reference herein.

The hydrophobic moiety, L, is typically a lipid such as a diacylglycerol, a sterol, a phospholipid, derivatives of these lipids, other naturally-occurring lipids and their synthetic analogs. The hydrophobic moiety is suitable for incorporation into a liposomal bilayer, to anchor the mitomycin C conjugate to a liposomal delivery vehicle.

The liposomal-mitomycin C prodrug conjugate upon exposure to reducing conditions, i.e., a reducing agent such as cysteine or glutathione, decomposes to yield mitomycin C. That is, thiolytic cleavage of the conjugate yields mitomycin C and non-toxic by products of the hydrophobic moiety and the dithiobenzyl moiety. As can be appreciated, the prodrug conjugate can be readily incorporated into liposomes for administration in vivo to a subject. The prodrug conjugate is not toxic, and after administration and upon exposure to endogenous reducing agents or exposure to an exogenous reducing agent, the conjugate decomposes to yield mitomycin C in its native state and with biological activity.

Studies conducted in support of the methods described herein used the prodrug conjugate para-diacyldiglyceroldithiobenzyl-mitomycin C. The prodrug conjugate ortho-diacyldiglyceroldithiobenzyl-mitomycin C can also be utilized. The conjugate was synthesized as set forth in Example 1. The conjugate is referred to herein as a "mitomycin C prodrug" or "mitomycin C prodrug conjugate" and is abbreviated in the drawings as "MLP" (mitomycin C liposomal prodrug conjugate).

The liposomes also comprise an anthracycline. Exemplary anthracyclines are doxorubicin, daunorubicin, epirubicin and idarubicin.

In one embodiment, the liposomes additionally comprise an ammonium salt. The ammonium salt provides a concentration of ammonium ions inside the liposomes, to establish a pH gradient from inside (lower) to outside (higher pH) the liposomes (i.e., a pH gradient across the liposomal lipid monolayer or bilayer(s)) in order to load into the liposomes an amphipathic or ionizable compound, such as an anthracycline drug. This method is detailed in U.S. Pat. No. 5,192,549, incorporated by reference herein. In one embodiment, the ammonium salt is an ammonium salt of a bisphosphonate. Examples include ammonium salts of alendronate, pamidronate, neridonate, olpadronate, ibandronate, risedronate and zoledronate. In another embodiment, the ammonium salt is an ammonium salt of sulfate, glucuronide, sucrose octasulfate (sucralfate), methanesulfonate, phosphate or dextran-sulfate. Loading of drugs using an alkyl or aryl sulfonate gradient, such as ammonium sucrose octasulfate (sucralfate) or an ammonium methanesulfonate gradient, is described in WO2013/114377, incorporated by reference herein.

Liposomes comprising the mitomycin C prodrug conjugate and the anthracycline drug doxorubicin were prepared as detailed in Example 1. The exemplary liposomes had an external coating of polyethylene glycol (PEG), as described, for example, in U.S. Pat. No. 5,013,556, incorporated by reference herein. The liposomes were prepared using hydrogenated soy phosphatidylcholine (HSPC), mPEG$_{2000}$-DSPE (methoxy-polyethylene glycol (MW 2,000 Daltons) attached to disteroylphosphatidylethanolamine), cholesterol and the mitomycin C prodrug conjugate at a percent molar ratio of 55:5:30:10, respectively. An ammonium salt of alendronate was encapsulated into the liposomes and then incubated with doxorubicin to load doxorubicin into the aqueous space of the liposomes. The liposomes with co-encapsulated doxorubicin, alendronate and mitomycin C prodrug were used in most of the studies now to be described. In another study, also described with respect to FIG. 11, liposomes with co-encapsulated doxorubicin and mitomycin C prodrug were prepared, where the doxorubicin was loaded into the liposomes using an ammonium sulfate gradient, rather than an alendronate sulfate gradient.

Figure 1C:
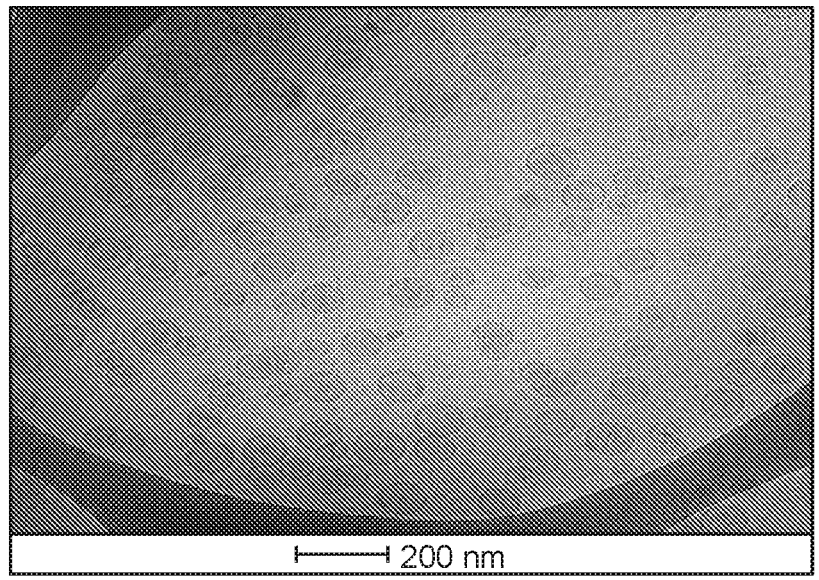
Figure 1D:
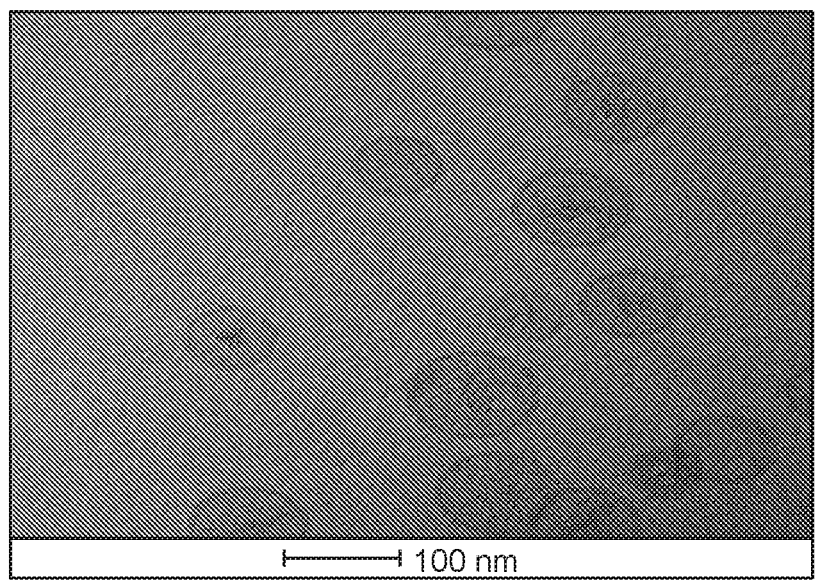

The liposomes with co-encapsulated doxorubicin and mitomycin C prodrug were inspected by electron cryomicroscopy (cryoTEM). The images are shown in FIGS. 1A-1D. A dominant population of spheroidal vesicles which are typically unilamellar liposomes of ≤100-nm diameter are seen. Precipitated crystals alendronate salt or doxorubicin salt in the interior water phase of the unilamellar vesicles is apparent (FIG. 1D). These precipitate formations are different from the rod-like formations previously reported for liposomes with doxorubicin loaded with ammonium sulfate but lacking the mitomycin C prodrug conjugate in the lipid bilayer (DOXIL) and for liposomes with doxorubicin loaded with ammonium alendronate but lacking the mitomycin C prodrug conjugate in the lipid bilayer. The precipitate in some liposomes has a star-like formation. Also some of the images, e.g., FIG. 1A, FIG. 1C, and FIG. 1D, show "kissing vesicles" with linear contact interface (rather than curvilinear). In some liposomes, electron-dense bands are found in the bilayer suggesting the presence of co-precipitates of doxorubicin-alendronate and mitomycin C prodrug conjugate.

Plasma stability of the liposomes with co-encapsulated doxorubicin-alendronate and mitomycin C prodrug was assessed as described in Example 2. Release of mitomycin C prodrug and of doxorubicin after incubation in human plasma was measured, and compared to release in buffer.

Figure 2A:
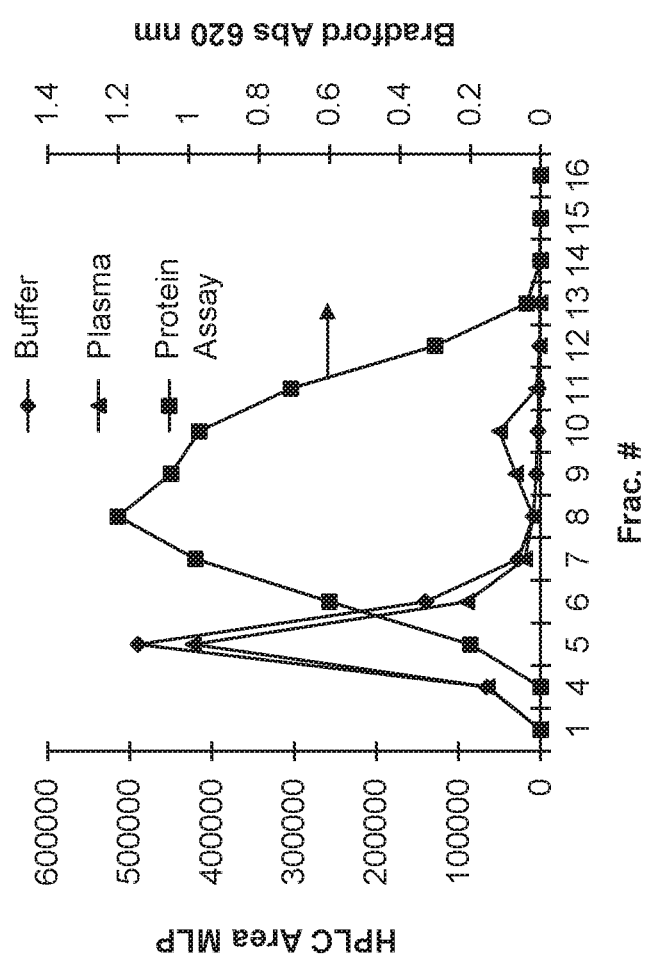
FIGS. 2A-2B show data from an assessment of liposome stability in plasma, where release of mitomycin C prodrug conjugate (abbreviated as MLP) (FIG. 2A) and of doxorubicin (abbreviated as Dox) (FIG. 2B) in fractions of eluent collected from a Sepharose column are shown following incubation of liposomes with co-encapsulated doxorubicin and mitomycin C prodrug conjugate in buffer (diamonds) and in human plasma (triangles). Elution of plasma protein was measured using the Bradford protein assay (absorbance at 620 nm, squares).
Figure 2B:
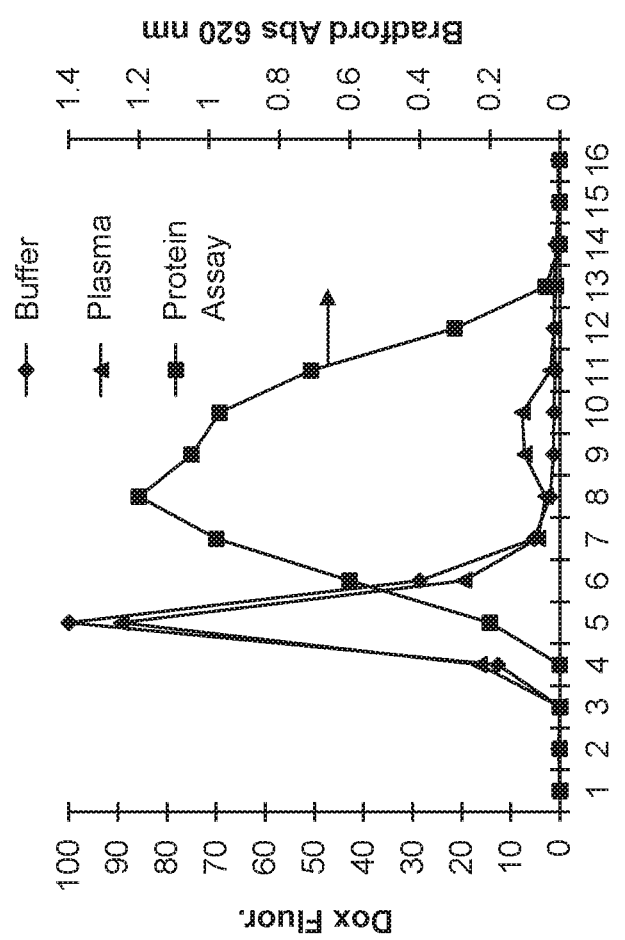

FIG. 2A shows the release of mitomycin C prodrug conjugate in fractions of eluent collected from the column after incubation of the liposomes in human plasma (triangles) and in buffer (diamonds). FIG. 2B is a similar graph showing release of doxorubicin in the eluent fractions after incubation of the liposomes in human plasma (triangles) and in buffer (diamonds). Elution of plasma protein was measured using the Bradford protein assay (absorbance at 620 nm, squares).

The data shows that liposomes elute in fractions 4-7, while nearly all the mitomycin C prodrug conjugate and the doxorubicin remain liposome-associated. Plasma proteins elute mostly in fractions 7-11. There was no significant mitomycin C prodrug conjugate or doxorubicin partitioning into plasma proteins and there was no detectable release of mitomycin C. Minimal overlap of mitomycin C prodrug conjugate or doxorubicin with plasma proteins was observed, and there was no late peak of free mitomycin C indicating that mitomycin C prodrug conjugate exchanges with proteins and/or that cleavage to free mitomycin C in plasma were insignificant. A small protein peak appearing in fraction 6 may be due to protein adsorption onto liposomes.

In another study conducted to evaluate the liposomes with co-encapsulated doxorubicin and mitomycin C prodrug, the cytotoxicity of the liposomes was evaluated in human cell lines, T24 bladder carcinoma, N87 gastric carcinoma and IGROV-1 ovarian carcinoma cells, the multidrug resistant M109R lung carcinoma cell line and in NCI/C. For comparison, liposomes with entrapped doxorubicin and a coating of polyethyleneglycol (PEG) (available under the tradename DOXIL®), liposomes with the mitomycin C prodrug conjugate incorporated into the lipid bilayer and a coating of PEG (sometimes referred to in the literature by the tradename PROMITIL®; sometimes referred to herein as liposomes-MLP or liposomes with mitomycin C prodrug conjugate) were also evaluated in the cell lines, along with free doxorubicin and liposomes with encapsulated doxorubicin-alendronate and a coating of PEG (U.S. 2014/0328899, incorporated by reference herein).

Details of the uptake studies are set forth in Example 3. In brief, the liposomal compositions or free doxorubicin were incubated for 3 hours with the cell lines at a doxorubicin concentration of 6.5 μmoles/L (3.7 μg/mL) and final mitomycin C lipid prodrug conjugate concentration of 5 μmoles/L (5.7 μg/mL).

Figure 3A:
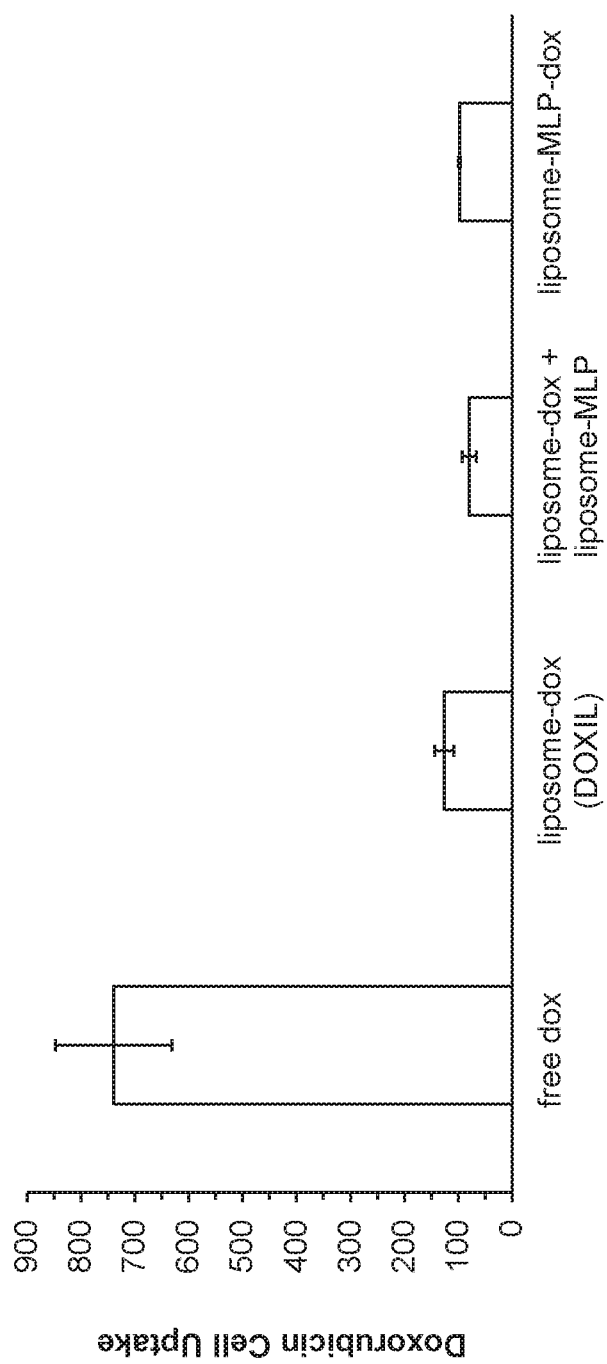
FIGS. 3A-3B are bar graphs showing the uptake of doxorubicin (FIG. 3A) and of mitomycin C prodrug (FIG. 3B) in T-24 bladder cancer cells incubated with free doxorubicin (free dox), liposomes with entrapped doxorubicin (liposome-dox, or DOXIL®, FIG. 3A only), a mixture of liposomes with mitomycin C prodrug conjugate (liposome-MLP or PROMITIL) and of liposomes with entrapped doxorubicin (liposome-dox, or DOXIL), liposomes with mitomycin C prodrug conjugate (liposome-MLP or PROMITIL, FIG. 3B only), and liposomes with co-encapsulated doxorubicin and mitomycin C prodrug (liposome-MLP-dox)
Figure 3B:
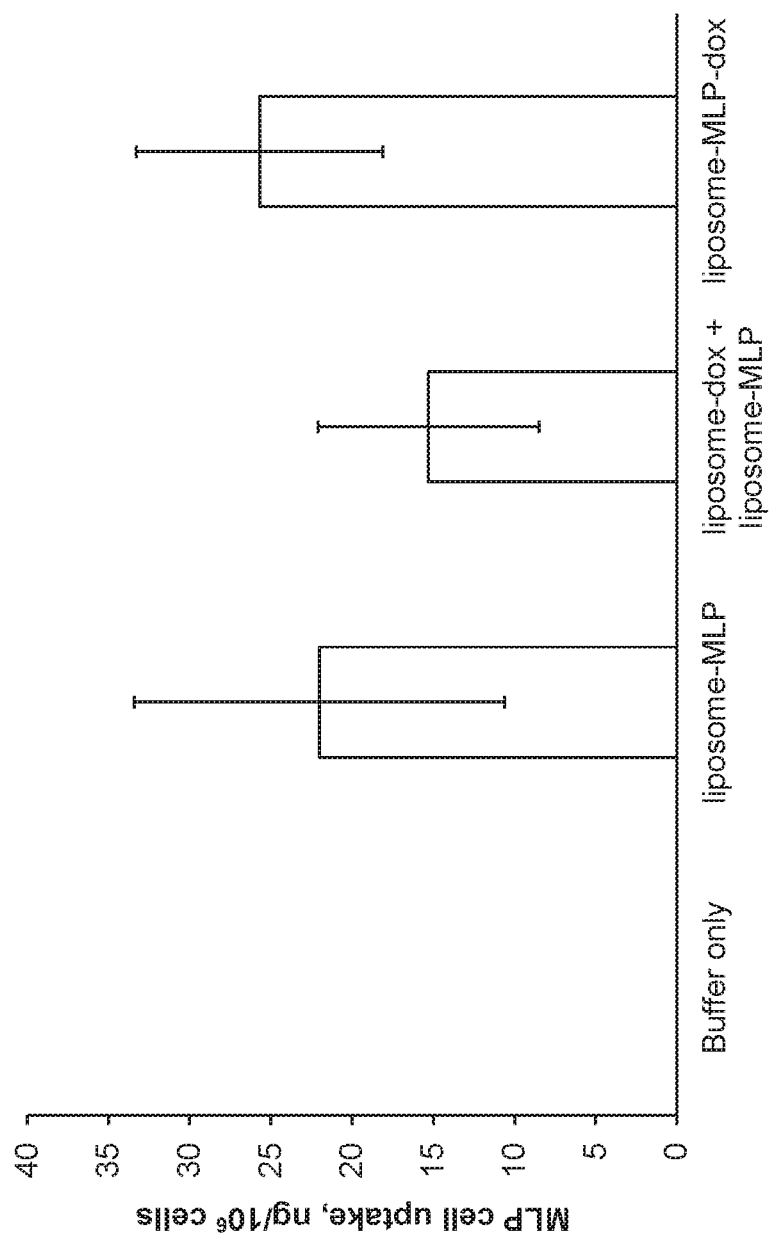
Figure 4A:
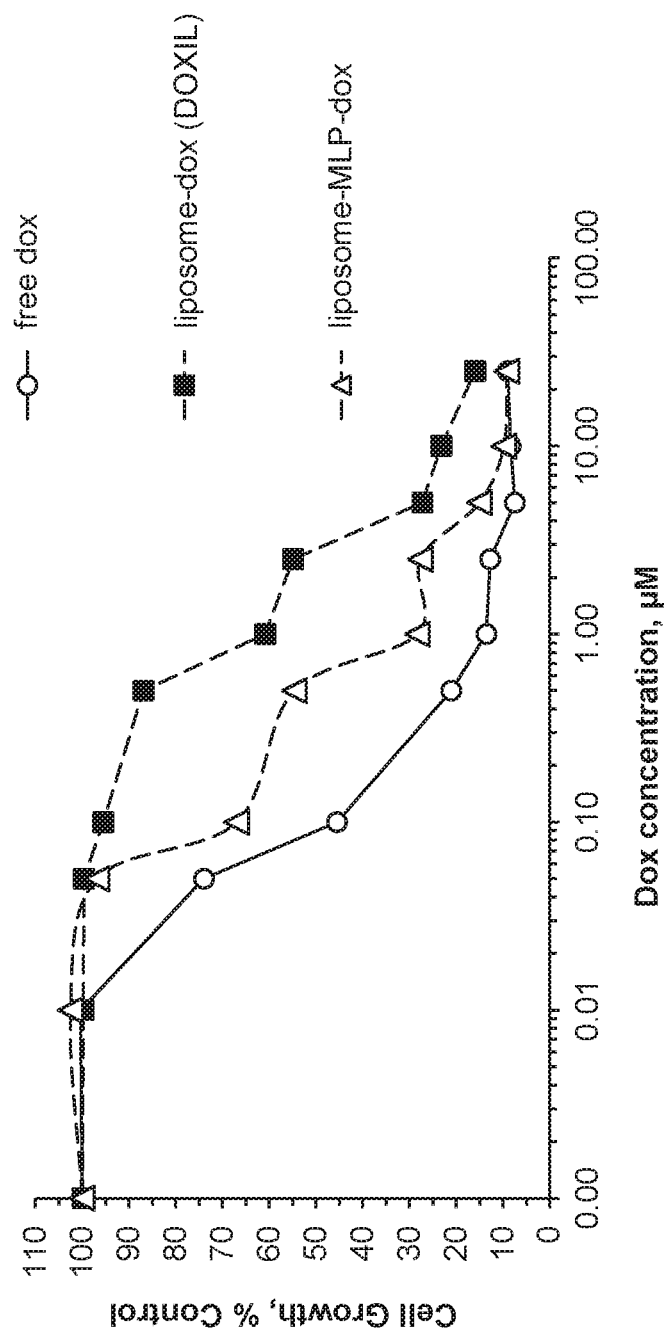
FIG. 4A is a graph from an in vitro cytotoxicity study, showing growth of T24 bladder cancer carcinoma cells, as a percentage of control (treated with buffer only) cells, as a function of doxorubicin concentration, in micromoles per liter (μM), after incubation for 72 hours at 37° C. with free doxorubicin (circles), liposomes with entrapped doxorubicin (liposome-dox or DOXIL, squares), and liposomes with co-encapsulated doxorubicin and mitomycin C prodrug (liposome-MLP-dox, triangles)
Figure 4B:
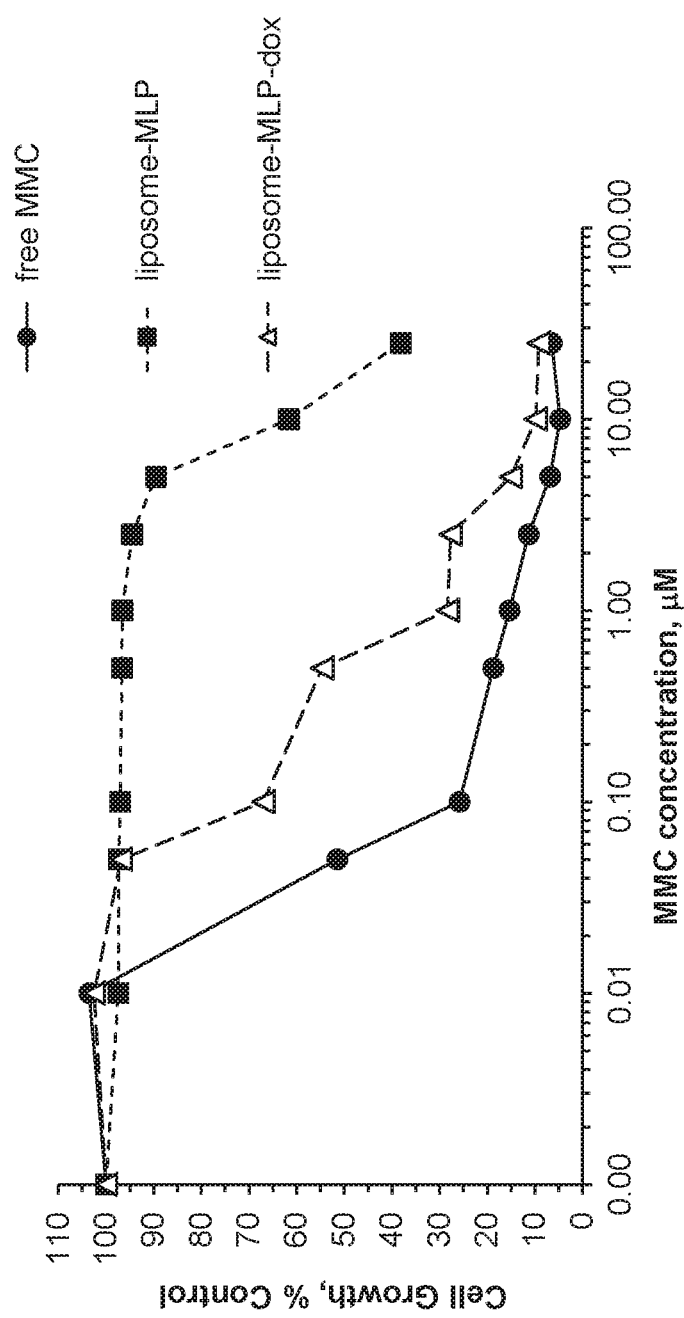
FIG. 4B is a graph from an in vitro cytotoxicity study, showing growth of T24 bladder cancer carcinoma cells, as a percentage of control cells, as a function of mitomycin C (MMC) concentration, in micromoles per liter (μM), after incubation for 72 hours at 37° C. with free mitomycin C (circles), liposomes with mitomycin C prodrug conjugate (liposome-MLP, squares), and liposomes with co-encapsulated doxorubicin and mitomycin C prodrug (liposome-MLP-dox, triangles)

Results for the study using T-24 bladder cancer cells are shown in FIG. 3A-3B and in the following table.

TABLE 1

Concentration of Doxorubicin and of mitomycin C prodrug conjugate in T-24 Bladder Cancer Cells after 3 hours of incubation

| Test Composition | Doxorubicin Concentration (ng/$10^6$ cells) | St. Dev. | Mitomycin C prodrug conjugate concentration (ng/$10^6$ cells) | St. Dev. |
|---|---|---|---|---|
| free doxorubicin | 739 | 108 | n/a | n/a |
| liposome-entrapped doxorubicin-sulfate (DOXIL). | 126 | 17.8 | n/a | n/a |
| liposome-entrapped doxorubicin-alendronate (PLAD) | 109 | 7.5 | n/a | n/a |
| liposomes with co-encapsulated doxorubicin and mitomycin C prodrug conjugate | 98 | 2.2 | 25.7 | 2.2 |
| liposomes with mitomycin C prodrug conjugate | n/a | n/a | 22 | 11.4 |

With reference to FIG. 3A, liposomes with co-encapsulated doxorubicin and mitomycin C prodrug, where doxorubicin was loaded into the liposomes against an ammonium alendronate gradient (Example 1) show a similar low cell uptake of doxorubicin as when the cells are treated with liposome-entrapped doxorubicin (compare bar labelled liposome-MLP-dox to bar labelled liposome-dox (DOXIL) in FIG. 3A), the low cell uptake of doxorubicin relative to the cell uptake when cells are treated with free doxorubicin. A mixture of liposomes with entrapped doxorubicin (liposome-dox) and of liposomes with mitomycin C prodrug conjugate (liposome-MLP) similarly provided a low cell uptake of doxorubicin, relative to that observed for treatment with free doxorubicin. The liposome compositions each resulted in a similar uptake of doxorubicin, which in all cases was lower than that of free doxorubicin.

When uptake of mitomycin C prodrug was examined (FIG. 3B), similar mitomycin C prodrug levels were measured in cells treated with liposomes with co-encapsulated doxorubicin and mitomycin C prodrug (liposome-MLP-dox) and cells treated with liposomes with the mitomycin C prodrug conjugate (liposome-MLP). Cells treated with a mixture of liposome-entrapped doxorubicin and liposomes with the mitomycin C prodrug conjugate achieved a similar uptake of mitomycin C prodrug conjugate. Free mitomycin C uptake into cells cannot be measured because the free drug rapidly interacts with cellular DNA undergoing a chemical change that renders it difficult to measure. Also, the level of mitomycin C prodrug conjugate in the cells is lower than that of doxorubicin because of the rapid cleavage of the mitomycin C prodrug conjugate into free mitomycin C and the aforementioned difficulty in measuring free mitomycin C in the cells.

The data in FIG. 3B reveals that treatment with liposomes with co-encapsulated doxorubicin and mitomycin C prodrug (liposome-MLP-dox) and with liposomes with the mitomycin C prodrug conjugate (liposome-MLP) result in comparable levels of mitomycin C prodrug conjugate in the cells. As will be shown below, the remarkable advantage of enhanced cytotoxicity of cells treated with liposomes co-encapsulated doxorubicin and mitomycin C prodrug is surprising in view of the mitomycin C prodrug conjugate cell uptake data. Similarly, the data in FIG. 3A reveals that treatment with liposomes with co-encapsulated doxorubicin and mitomycin C prodrug (liposome-MLP-dox) and with liposomes with the mitomycin C prodrug conjugate (liposome-MLP) result in comparable levels of doxorubicin in the cells. As will be shown below, the remarkable advantage of enhanced cytotoxicity of cells treated with liposomes co-encapsulated doxorubicin and mitomycin C prodrug is surprising in view of the doxorubicin cell uptake data suggesting no difference in drug uptake when administered as liposome-entrapped doxorubicin or liposomes with co-encapsulated doxorubicin and mitomycin C prodrug.

The in vitro cytotoxicity results are shown in FIGS. 4-9. With initial reference to FIG. 4A, growth of T24 bladder cancer carcinoma cells, as a percentage of control cells, as a function of doxorubicin concentration, in micromoles per liter, after incubation for 72 hours at 37° C. with free doxorubicin (circles), liposomes with entrapped doxorubicin (DOXIL, squares), and liposomes with co-encapsulated doxorubicin and mitomycin C prodrug (triangles) is shown. FIG. 4B is a similar graph for the study with T24 bladder cancer carcinoma cells where cell growth is shown as a function of mitomycin C (MMC) concentration, in micromoles per liter, after incubation with free mitomycin C (circles), liposomes with mitomycin C prodrug (squares), and liposomes with co-encapsulated doxorubicin and mitomycin C prodrug (triangles). Liposomes with co-encapsulated doxorubicin and mitomycin C prodrug were more cytotoxic to the cells than was treatment with a mixture of liposomes with entrapped doxorubicin (DOXIL) and liposomes with entrapped mitomycin C prodrug conjugate. Remarkably, treatment liposomes with co-encapsulated doxorubicin and mitomycin C prodrug was approximately as cytotoxic as treatment with free doxorubicin or with free mitomycin C. The $IC_{50}$ values in the T-24 cells are shown in Table 2.

TABLE 2

$IC_{50}$ values of doxorubicin and of mitomycin C in T24 cells.

| Test Agent | $C_{50}$ of doxorubicin (μM) | $IC_{50}$ of Mitomycin C (μM) |
|---|---|---|
| free mitomycin C | | 0.05 |
| free doxorubicin | 0.1 | |
| liposomes with entrapped doxorubicin (DOXIL) | 2.95 | |
| liposomes with mitomycin C prodrug (MLP) | | 17.4 |
| liposomes with co-encapsulated doxorubicin and mitomycin C prodrug | 0.6 | 0.5 |

Figure 5A:
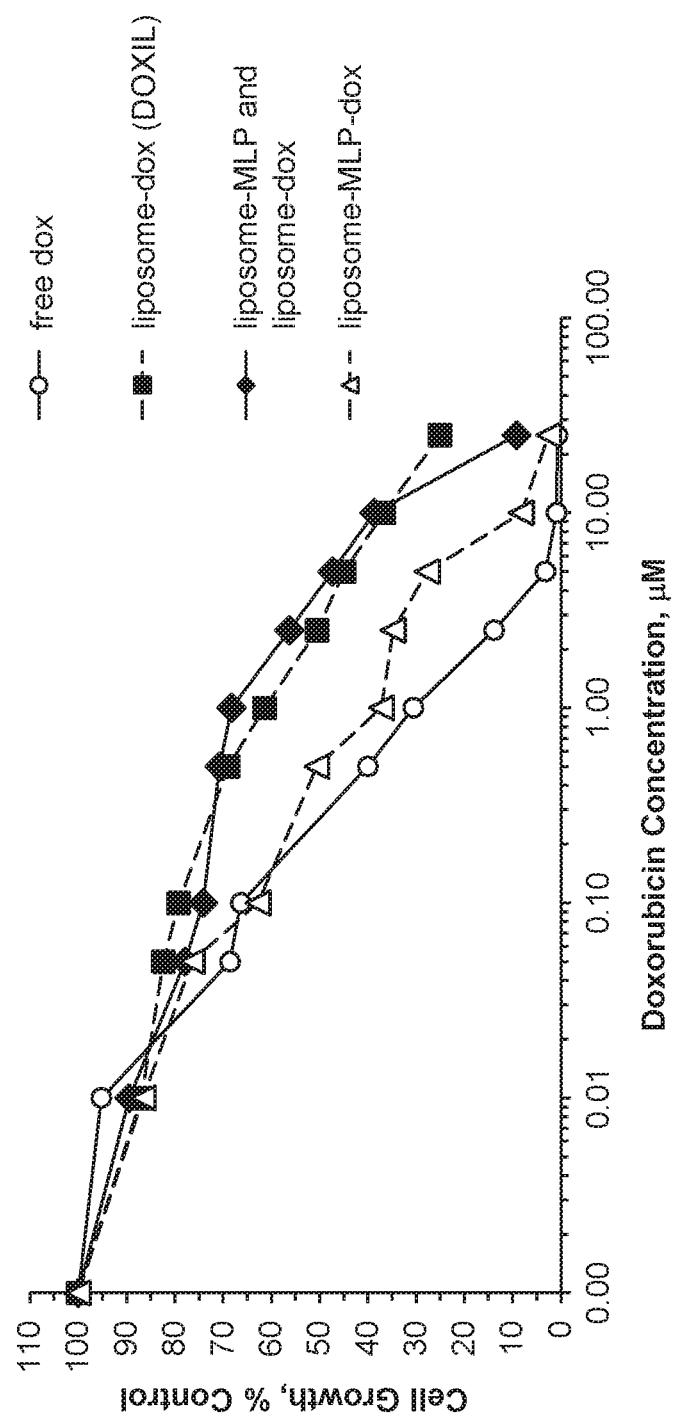
FIG. 5A is a graph from an in vitro cytotoxicity study, showing growth of N-87 gastric carcinoma cells, as a percentage of control cells, as a function of doxorubicin concentration, in micromoles per liter (μM), after incubation for 72 hours at 37° C. with free doxorubicin (circles), liposomes with entrapped doxorubicin (liposome-dox or DOXIL, squares), a mixture of liposomes with mitomycin C prodrug (liposome-MLP or PROMITIL) and liposomes with entrapped doxorubicin (liposome-dox or DOXIL) (diamonds), and liposomes with co-encapsulated doxorubicin and mitomycin C prodrug (triangles)
Figure 5B:
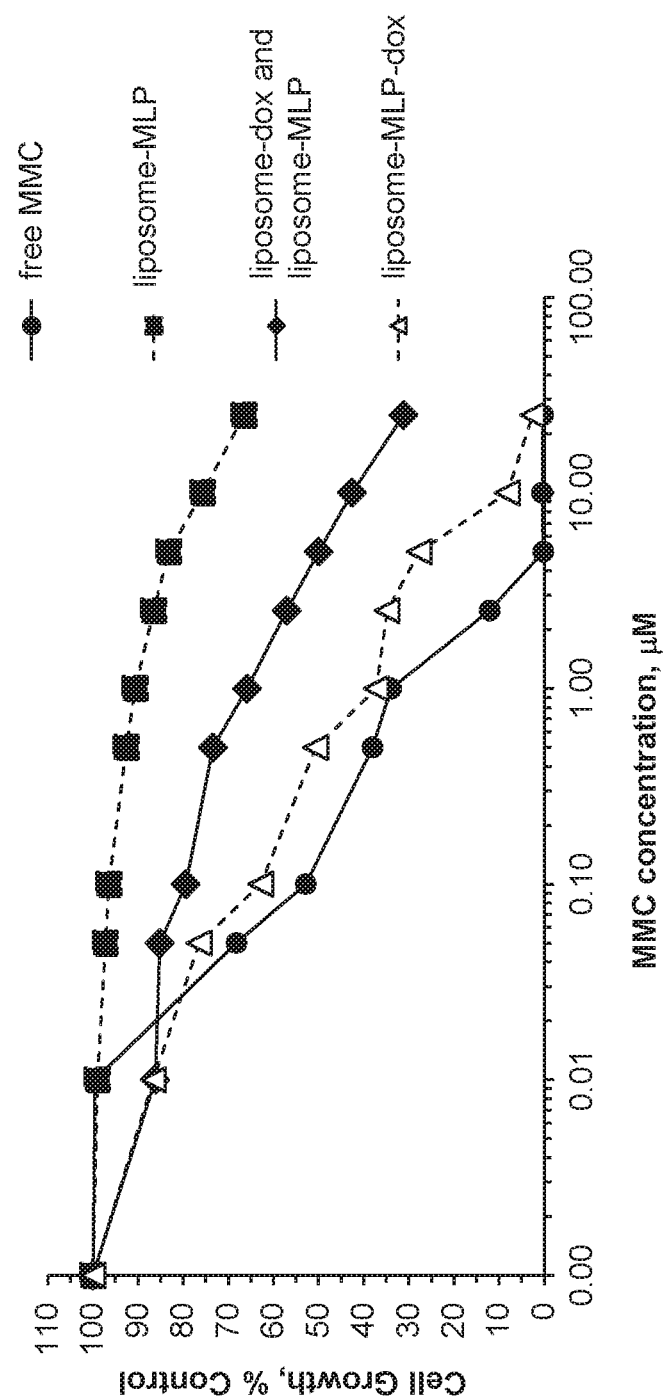
FIG. 5B is a graph from an in vitro cytotoxicity study, showing growth of N-87 gastric carcinoma cells, as a percentage of control cells, as a function of mitomycin C (MMC) concentration, in micromoles per liter (μM), after incubation for 72 hours at 37° C. with free mitomycin C (circles), liposomes with mitomycin C prodrug (squares), a mixture of liposomes with entrapped doxorubicin and of liposomes with mitomycin C prodrug, (diamonds), and liposomes with co-encapsulated doxorubicin and mitomycin C prodrug (triangles)

Results of the cytotoxicity test using human N-87 gastric carcinoma cells are shown in FIGS. 5A-5B and in Table 3. FIG. 5A shows growth of N-87 gastric carcinoma cells, as a percentage of control cells, as a function of doxorubicin concentration, in micromoles, after incubation for 72 hours at 37° C. with free doxorubicin (circles), liposomes with entrapped doxorubicin (DOXIL, squares), a mixture of liposomes with mitomycin C prodrug (liposome-MLP, PROMITIL) and liposomes with entrapped doxorubicin (liposome-dox, DOXIL) (diamonds), and liposomes with co-encapsulated doxorubicin and mitomycin C prodrug (triangles). FIG. 5B shows the results for mitomycin C, for growth of N-87 gastric carcinoma cells as a function of mitomycin C (MMC) concentration, in micromoles, after incubation for 72 hours at 37° C. with free mitomycin C (circles), liposomes with mitomycin C prodrug (squares), a mixture of liposomes with entrapped doxorubicin and of liposomes with mitomycin C prodrug (diamonds), and liposomes with co-encapsulated doxorubicin and mitomycin C prodrug (triangles). Liposomes with co-encapsulated doxorubicin and mitomycin C prodrug provide a much higher cytotoxicity activity than liposomes with the mitomycin C prodrug conjugate, or a combination of liposomes with mitomycin C prodrug conjugate and of liposomes with entrapped doxorubicin (DOXIL), and nearly equal activity to the free drugs, doxorubicin and mitomycin C.

TABLE 3

$IC_{50}$ values of doxorubicin and of mitomycin C in N-87 gastric carcinoma cells.

| Test Agent | $IC_{50}$ of doxorubicin (μM) | $IC_{50}$ of Mitomycin C (μM) |
|---|---|---|
| free mitomycin C | | 0.18 |
| free doxorubicin | 0.19 | |
| liposomes with entrapped doxorubicin (DOXIL) | 2.7 | |
| liposomes with the mitomycin C prodrug conjugate (PROMITIL) | | 16.3 |
| combination of PROMITIL + DOXIL | 4.3 | 3.6 |
| combination of liposomes with mitomycin C prodrug conjugate and of liposomes with entrapped doxorubicin (DOXIL) | 5 | 4.2 |
| liposomes with co-encapsulated doxorubicin and mitomycin C prodrug | 0.5 | 0.4 |

Figure 6A:
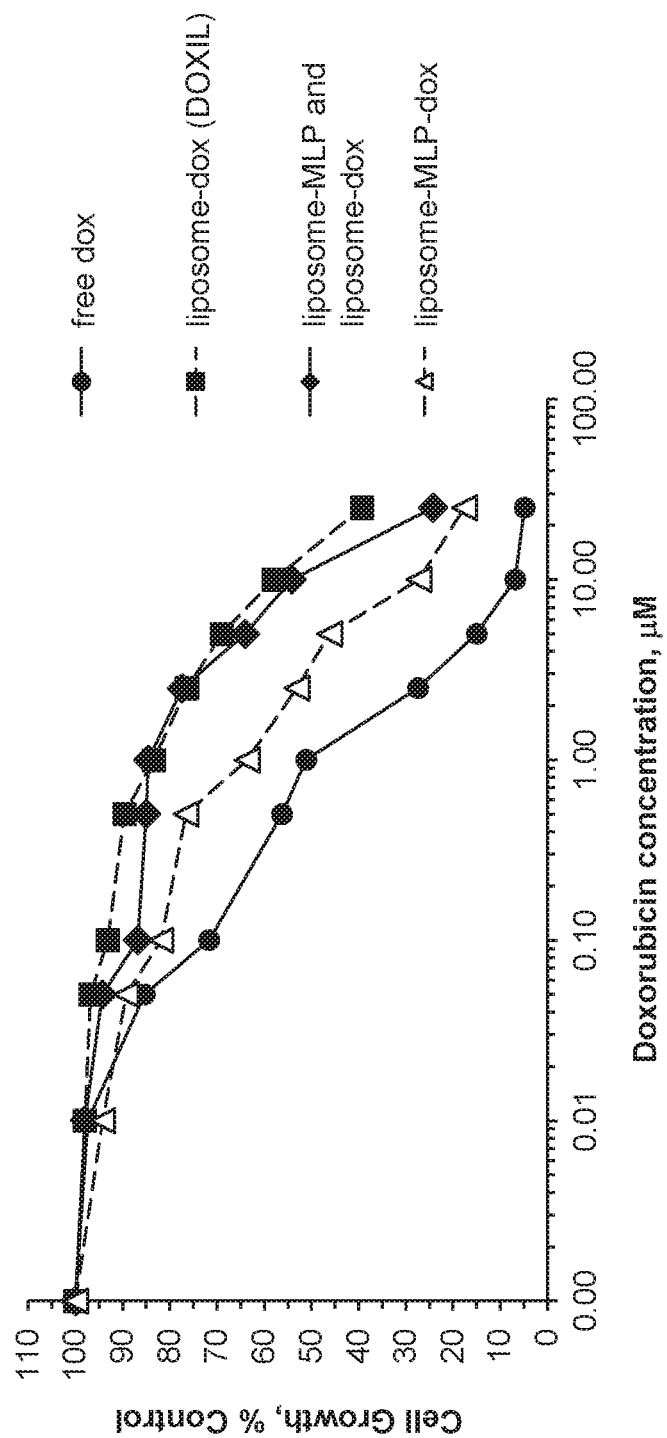
FIG. 6A is a graph from an in vitro cytotoxicity study, showing growth of IGrov-1 ovarian carcinoma cells, as a percentage of control cells, as a function of doxorubicin concentration, in micromoles per liter (μM), after incubation for 72 hours at 37° C. with free doxorubicin (circles), liposomes with entrapped doxorubicin (DOXIL, squares), a mixture of liposomes with mitomycin C prodrug (PROMITIL) and liposomes with entrapped doxorubicin (DOXIL) (diamonds), and liposomes with co-encapsulated doxorubicin and mitomycin C prodrug (triangles)
Figure 6B:
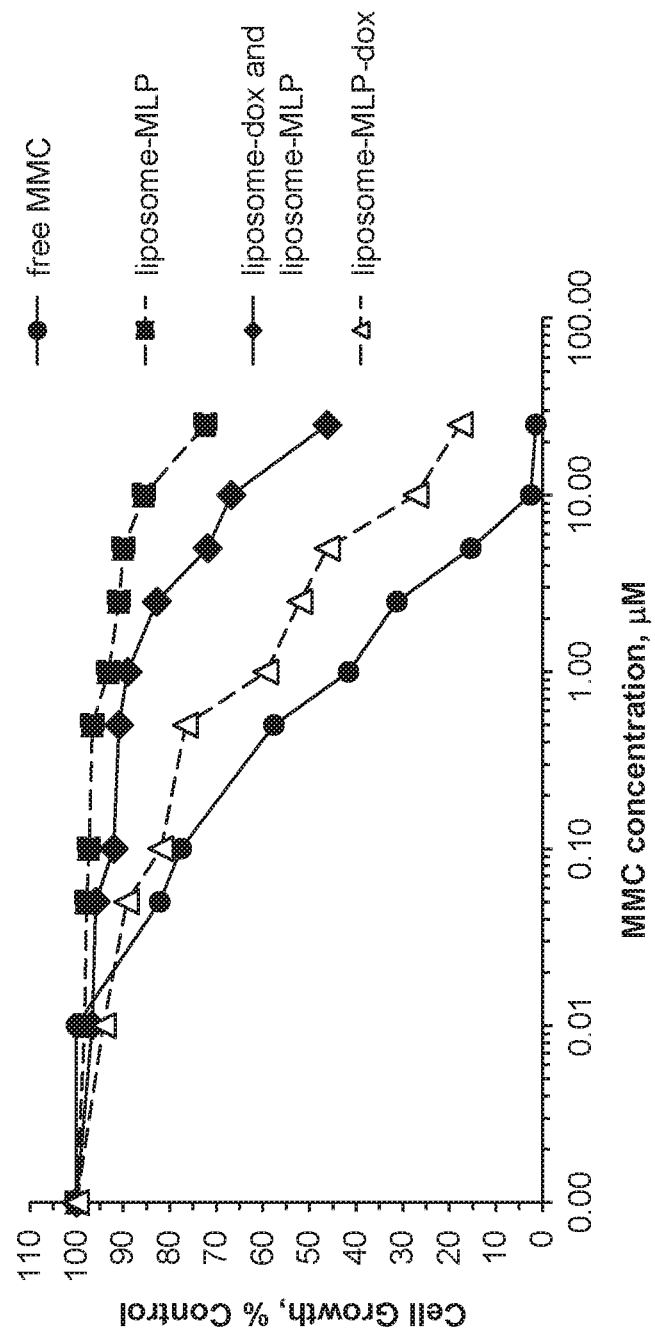
FIG. 6B is a graph from an in vitro cytotoxicity study, showing growth of IGrov-1 ovarian carcinoma cells, as a percentage of control cells, as a function of mitomycin C (MMC) concentration, in micromoles per liter (μM), after incubation for 72 hours at 37° C. with free mitomycin C (circles), liposomes with mitomycin C prodrug (squares), a mixture of liposomes with entrapped doxorubicin and of liposomes with mitomycin C prodrug, (diamonds), and liposomes with co-encapsulated doxorubicin and mitomycin C prodrug (triangles)

Similar results were obtained in IGROV-1 cells, as seen in FIGS. 6A-6B and Table 4. FIG. 6A is a graph from an in vitro cytotoxicity study, showing growth of IGrov-1 ovarian carcinoma cells, as a percentage of control cells, as a function of doxorubicin concentration, in micromoles, after incubation for 72 hours at 37° C. with free doxorubicin (circles), liposomes with entrapped doxorubicin (DOXIL, squares), a mixture of liposomes with mitomycin C prodrug (PROMITIL) and liposomes with entrapped doxorubicin (DOXIL) (diamonds), and liposomes with co-encapsulated doxorubicin and mitomycin C prodrug (triangles).

FIG. 6B is a graph from an in vitro cytotoxicity study, showing growth of IGrov-1 ovarian carcinoma cells, as a percentage of control cells, as a function of mitomycin C (MMC) concentration, in micromoles, after incubation for 72 hours at 37° C. with free mitomycin C (circles), liposomes with mitomycin C prodrug (squares), a mixture of liposomes with entrapped doxorubicin and of liposomes with mitomycin C prodrug, (diamonds), and liposomes with co-encapsulated doxorubicin and mitomycin C prodrug (triangles).

TABLE 4

$IC_{50}$ values of doxorubicin and of mitomycin C in IGrov-1 ovarian carcinoma cells.

| Test Agent | $IC_{50}$ of doxorubicin (μM) | $IC_{50}$ of Mitomycin C (μM) |
|---|---|---|
| free mitomycin C | | 0.7 |
| free doxorubicin | 1.1 | |
| liposomes with entrapped doxorubicin (DOXIL) | 16.4 | |
| liposomes with the mitomycin C prodrug conjugate (PROMITIL) | | 18.3 |
| combination of PROMITIL + DOXIL | 12.1 | 10 |
| combination of liposomes with mitomycin C prodrug conjugate and of liposomes with entrapped doxorubicin (DOXIL) | 21.1 | 17.6 |
| liposomes with co-encapsulated doxorubicin and mitomycin C prodrug | 3.4 | 2.8 |

Figure 7A:
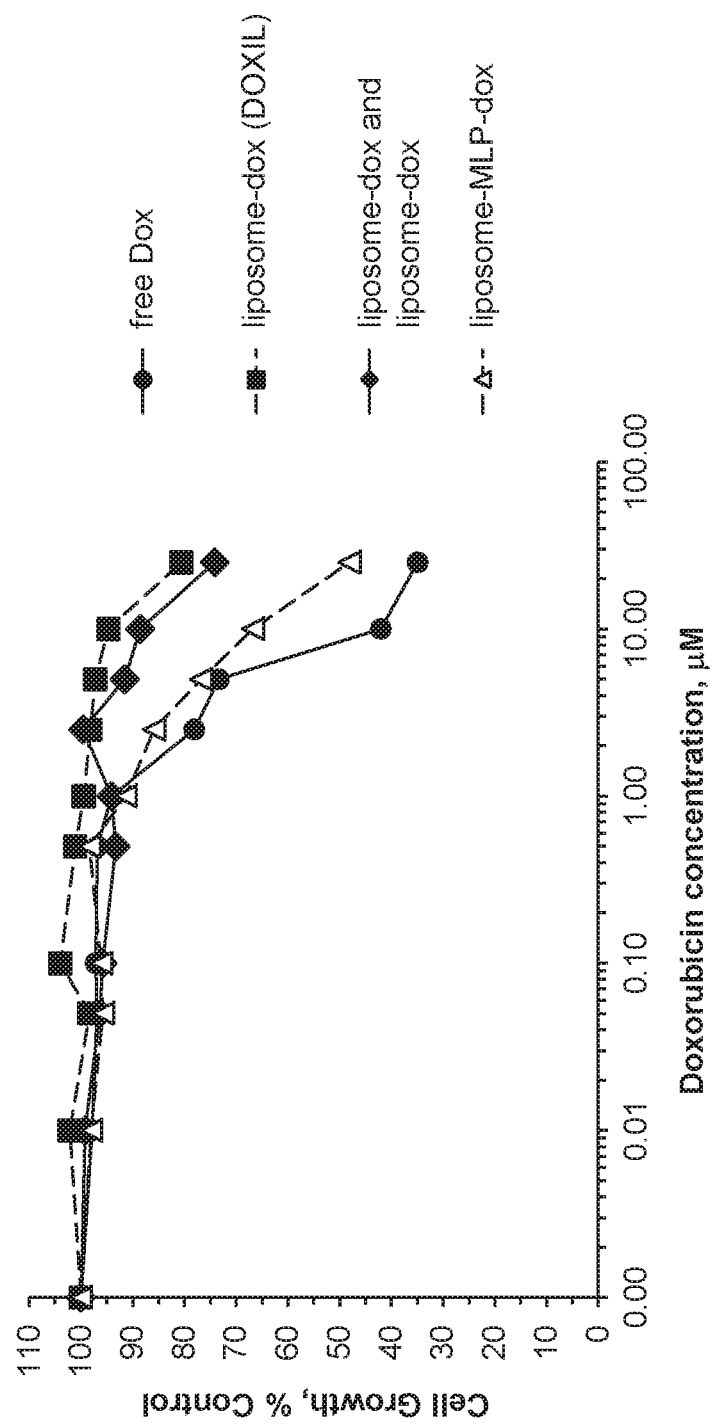
FIG. 7A is a graph from an in vitro cytotoxicity study, showing growth of multidrug resistant M109R lung carcinoma cells, as a percentage of control cells, as a function of doxorubicin concentration, in micromoles per liter (μM), after incubation for 72 hours at 37° C. with free doxorubicin (circles), liposomes with entrapped doxorubicin (DOXIL, squares), a mixture of liposomes with mitomycin C prodrug (PROMITIL) and liposomes with entrapped doxorubicin (DOXIL) (diamonds), and liposomes with co-encapsulated doxorubicin and mitomycin C prodrug (triangles)
Figure 7B:
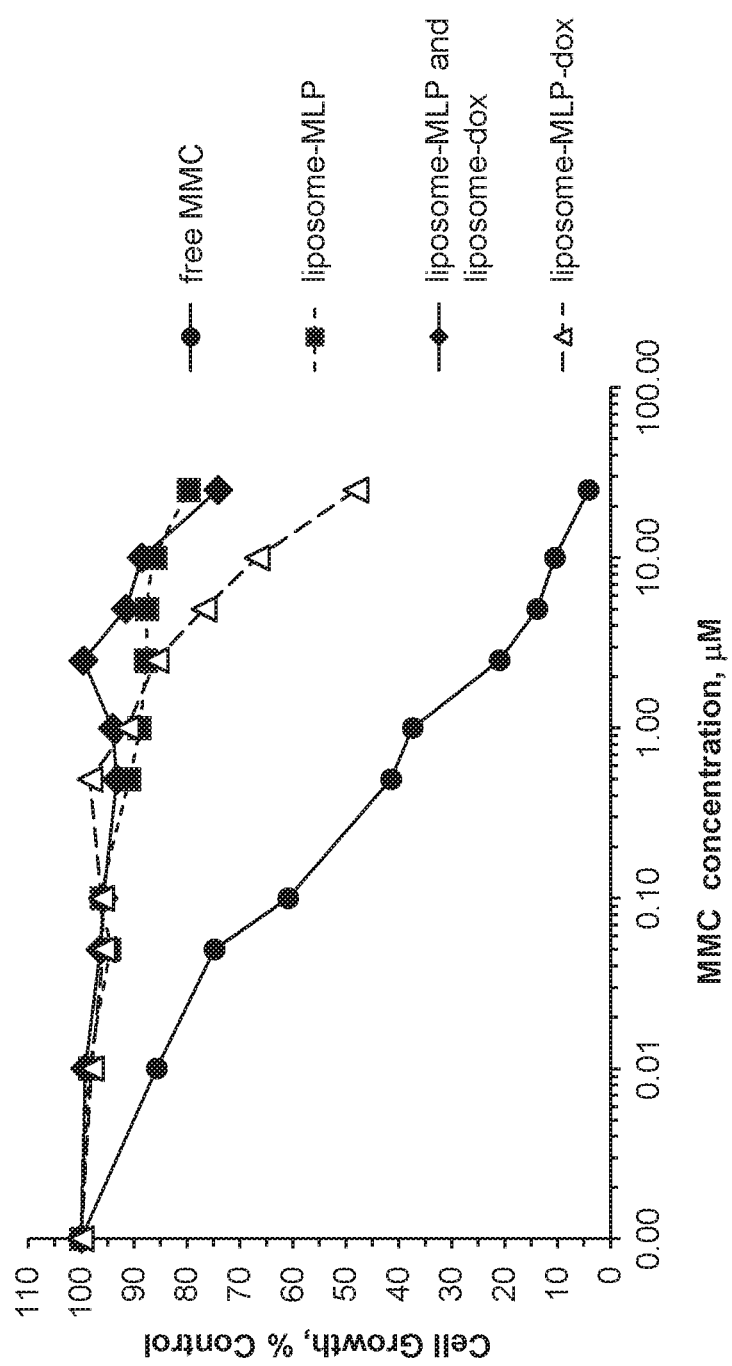
FIG. 7B is a graph from an in vitro cytotoxicity study, showing growth of multidrug resistant M109R lung carcinoma cells, as a percentage of control cells, as a function of mitomycin C (MMC) concentration, in micromoles per liter (μM), after incubation for 72 hours at 37° C. with free mitomycin C (circles), liposomes with mitomycin C prodrug (squares), a mixture of liposomes with entrapped doxorubicin and of liposomes with co-encapsulated alendronate and mitomycin C prodrug, (diamonds), and liposomes with co-encapsulated doxorubicin and mitomycin C prodrug, the doxorubicin loaded using an ammonium alendronate ion gradient (triangles)

Results of the cytotoxicity test using multidrug resistant M109R lung carcinoma cells are shown in FIGS. 7A-7B and in Table 5. FIG. 7A shows growth of multidrug resistant M109R lung carcinoma cells, as a percentage of control cells, as a function of doxorubicin concentration, in micromoles, after incubation for 72 hours at 37° C. with free doxorubicin (circles), liposomes with entrapped doxorubicin (DOXIL, squares), a mixture of liposomes with mitomycin C prodrug (PROMITIL) and liposomes with entrapped doxorubicin (DOXIL) (diamonds), and liposomes with co-encapsulated doxorubicin and mitomycin C prodrug (triangles). FIG. 7B shows growth of multidrug resistant M109R lung carcinoma cells, as a percentage of control cells, as a function of mitomycin C (MMC) concentration, in micromoles, after incubation for 72 hours at 37° C. with free mitomycin C (circles), liposomes with mitomycin C prodrug (squares), a mixture of liposomes with entrapped doxorubicin and of liposomes with mitomycin C prodrug, (diamonds), and liposomes with co-encapsulated doxorubicin and mitomycin C prodrug (triangles). As expected for M109R lung carcinoma cells, the cells are resistant to the doxorubicin in the liposomes with entrapped doxorubicin (DOXIL) and to the mitomycin C in liposomes with the mitomycin C prodrug conjugate (PROMITIL). However, the liposomes with co-encapsulated doxorubicin and mitomycin C prodrug show an enhanced cytotoxicity, even compared to cells incubated with a mixture of liposomes with entrapped doxorubicin (DOXIL) and liposomes with the mitomycin C prodrug conjugate (PROMITIL).

TABLE 5

$IC_{50}$ values of doxorubicin and of mitomycin C in multidrug resistant M109R lung carcinoma cells.

| Test Agent | $IC_{50}$ of doxorubicin (μM) | $IC_{50}$ of Mitomycin C (μM) |
|---|---|---|
| free mitomycin C | | 0.3 |
| free doxorubicin | 8.7 | |
| liposomes with entrapped doxorubicin (DOXIL) | >25 | |
| liposomes with the mitomycin C prodrug conjugate (PROMITIL) | | >25 |
| combination of PROMITIL + DOXIL | >25 | >25 |
| combination of liposomes with mitomycin C prodrug conjugate and of liposomes with entrapped doxorubicin (DOXIL) | >25 | >25 |
| liposomes with co-encapsulated doxorubicin and mitomycin C prodrug | 22.8 | 19.5 |

Figure 8A:
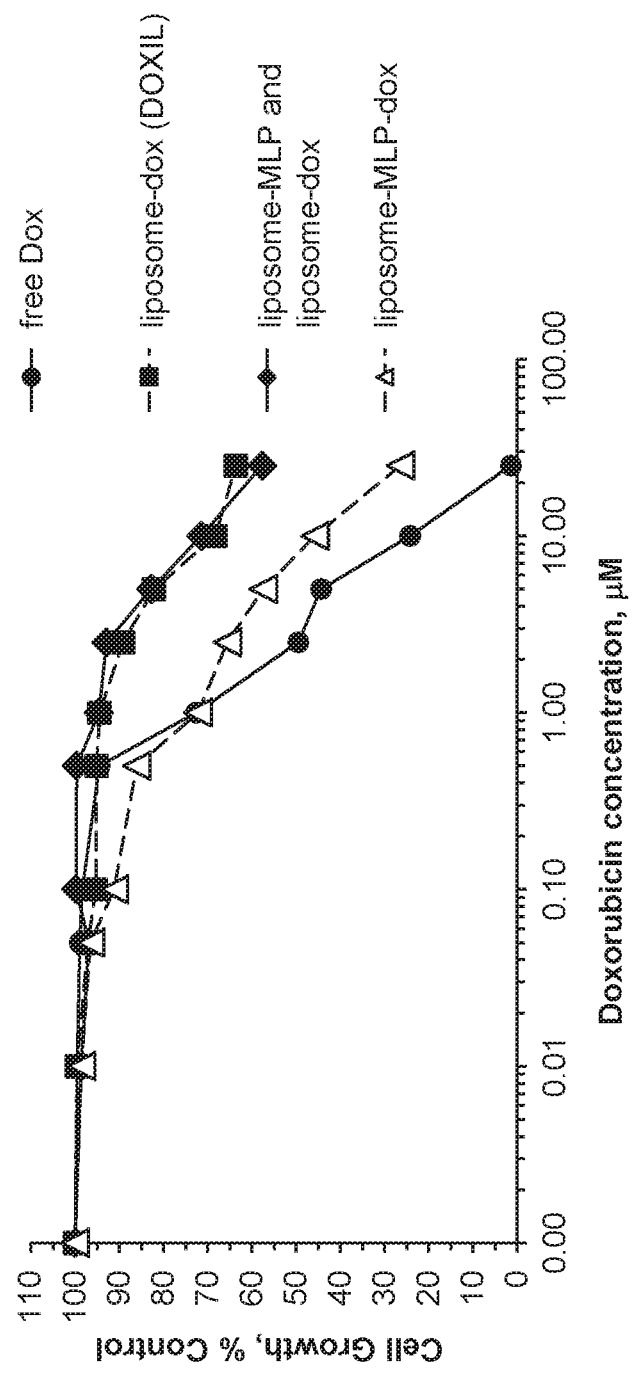
FIG. 8A is a graph from an in vitro cytotoxicity study, showing growth of NCI/ADR cells, as a percentage of control cells, as a function of doxorubicin concentration, in micromoles per liter (μM), after incubation for 72 hours at 37° C. with free doxorubicin (circles), liposomes with entrapped doxorubicin (DOXIL, squares), a mixture of liposomes with mitomycin C prodrug (PROMITIL) and liposomes with entrapped doxorubicin (DOXIL) (diamonds), and liposomes with co-encapsulated doxorubicin and mitomycin C prodrug (triangles)
Figure 8B:
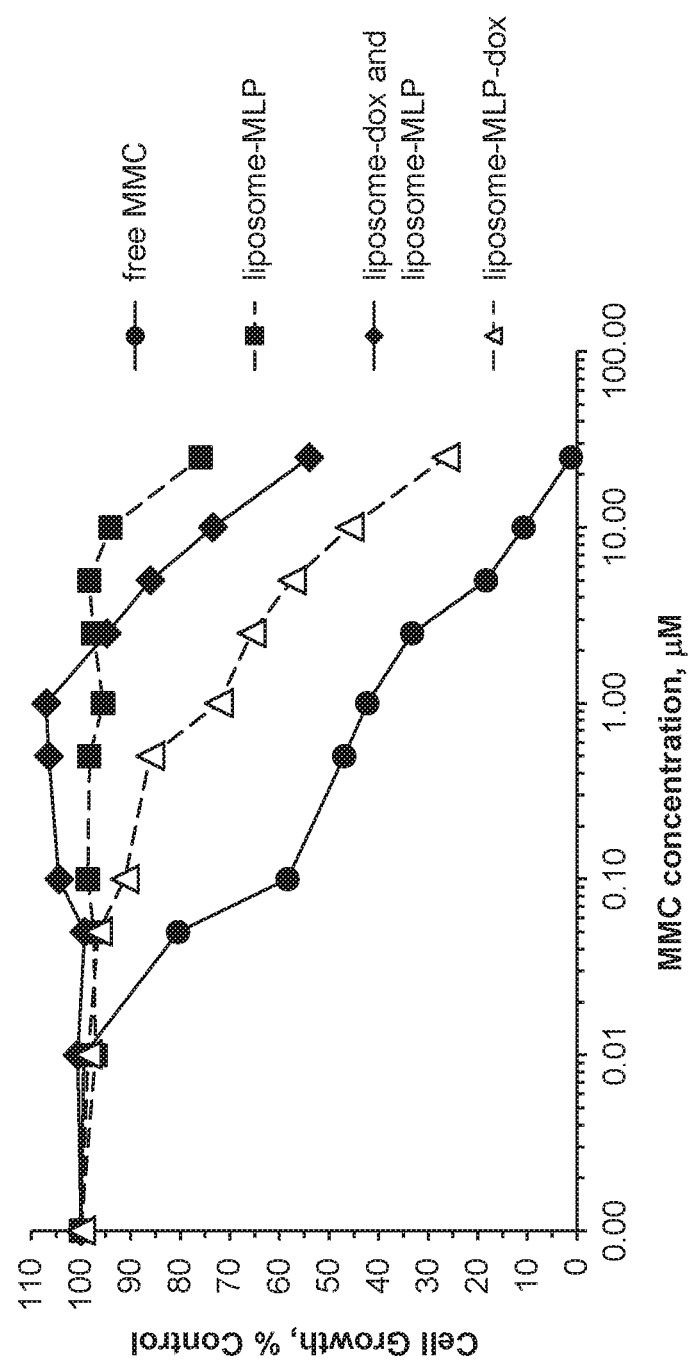
FIG. 8B is a graph from an in vitro cytotoxicity study, showing growth of NCI/ADR cells, as a percentage of control cells, as a function of mitomycin C (MMC) concentration, in micromoles per liter (μM), after incubation for 72 hours at 37° C. with free mitomycin C (circles), liposomes with mitomycin C prodrug (squares), a mixture of liposomes with entrapped doxorubicin and of liposomes mitomycin C prodrug, (diamonds), and liposomes with co-encapsulated doxorubicin and mitomycin C prodrug (triangles)

Results of the cytotoxicity test using multidrug resistant NCI/ADR ovarian carcinoma cells are shown in FIGS. 8A-8B and in Table 6. FIG. 8A shows growth of NCI/ADR cells, as a percentage of control cells, as a function of doxorubicin concentration, in micromoles, after incubation for 72 hours at 37° C. with free doxorubicin (circles), liposomes with entrapped doxorubicin (DOXIL, squares), a mixture of liposomes with mitomycin C prodrug (PROMITIL) and liposomes with entrapped doxorubicin (DOXIL) (diamonds), and liposomes with co-encapsulated doxorubicin and mitomycin C prodrug (triangles). FIG. 8B shows growth of NCI/ADR cells, as a percentage of control cells, as a function of mitomycin C (MMC) concentration, in micromoles, after incubation for 72 hours at 37° C. with free mitomycin C (circles), liposomes with mitomycin C prodrug (squares), a mixture of liposomes with entrapped doxorubicin and of liposomes with mitomycin C prodrug, (diamonds), and liposomes with co-encapsulated doxorubicin and mitomycin C prodrug (triangles). It is interesting to note that liposomes with co-encapsulated doxorubicin and mitomycin C prodrug are more cytotoxic to the cells that are liposomes with doxorubicin (DOXIL), or liposomes with mitomycin C prodrug conjugate (PROMITIL), and or a mixture of liposomes with doxorubicin and of liposomes with mitomycin C prodrug conjugate. Remarkably, the cytotoxicity achieved with liposomes with co-encapsulated doxorubicin and mitomycin C prodrug approximates the cytotoxic activity of free doxorubicin in NCI/ADR carcinoma cells. These results clearly show a synergistic cytotoxicity contribution when the mitomycin C prodrug-conjugate and doxorubicin are co-encapsulated in a liposome vehicle.

TABLE 6

$IC_{50}$ of doxorubicin and of mitomycin C NCI/ADR cells

| Test Agent | $IC_{50}$ of doxorubicin (μM) | $IC_{50}$ of Mitomycin C (μM) |
|---|---|---|
| free mitomycin C | | 0.4 |
| free doxorubicin | 2.5 | |
| liposomes with entrapped doxorubicin (DOXIL) | >25 | |
| liposomes with the mitomycin C prodrug conjugate (PROMITIL) | | >25 |
| combination of PROMITIL + DOXIL | >25 | >25 |
| combination of liposomes with mitomycin C prodrug conjugate and of liposomes with entrapped doxorubicin (DOXIL) | >25 | >25 |
| liposomes with co-encapsulated doxorubicin and mitomycin C prodrug | 7.8 | 6.6 |

Figure 9A:
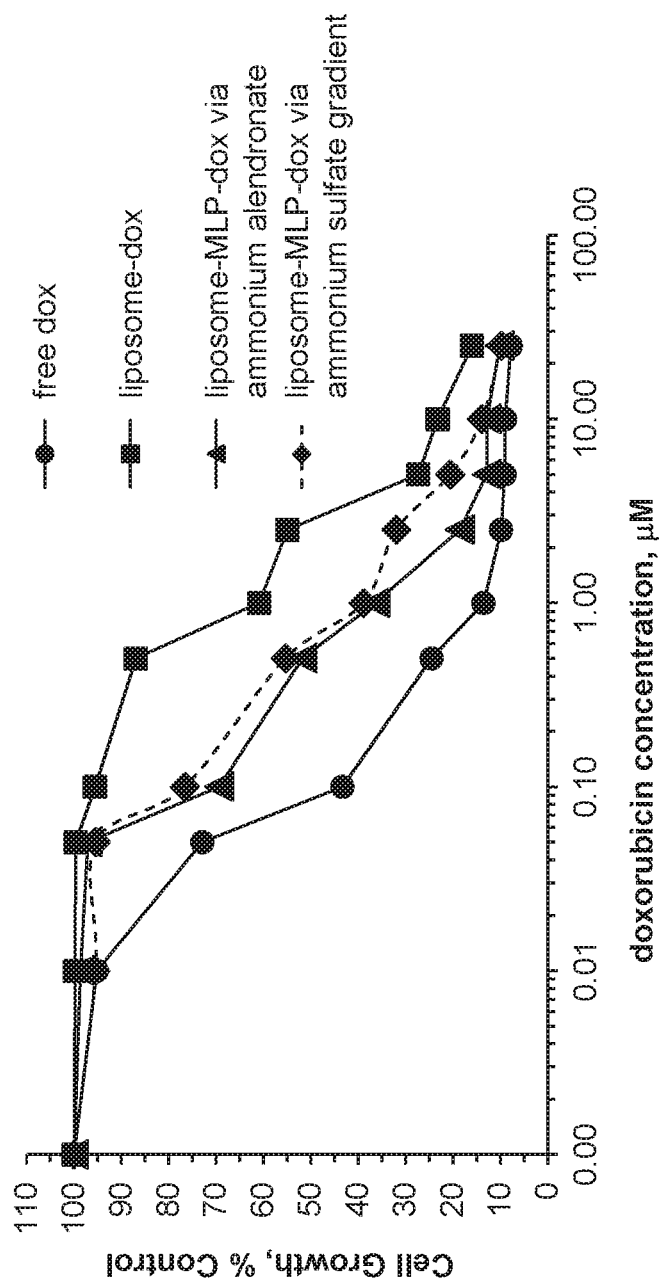
FIG. 9A is a graph from an in vitro cytotoxicity study, showing growth of T24 bladder cancer carcinoma cells, as a percentage of control cells (untreated), as a function of doxorubicin concentration, in micromoles per liter (μM), after incubation for 72 hours at 37° C. with free doxorubicin (circles), liposomes with entrapped doxorubicin (liposome-dox, DOXIL, squares), liposomes with co-encapsulated doxorubicin and mitomycin C prodrug, the doxorubicin loaded into the liposomes using an ammonium alendronate gradient (triangles), and liposomes with co-encapsulated doxorubicin and mitomycin C prodrug, the doxorubicin loaded into the liposomes using an ammonium sulfate gradient (diamonds)
Figure 9B:
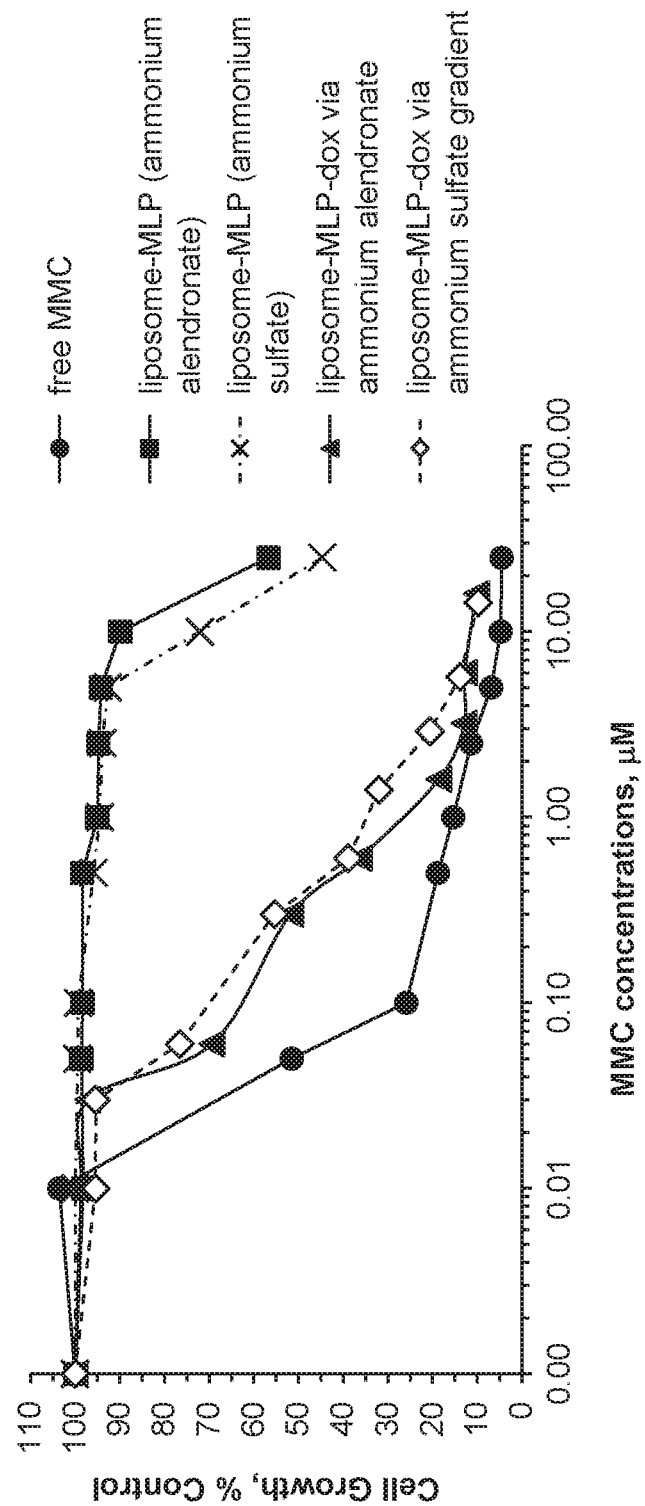
FIG. 9B is a graph from an in vitro cytotoxicity study, showing growth of T24 bladder cancer carcinoma cells, as a percentage of control (untreated) cells, as a function of mitomycin C (MMC) concentration, in micromoles per liter (μM), after incubation for 72 hours at 37° C. with free mitomycin C (circles), liposomes with mitomycin C prodrug and ammonium-alendronate (squares), liposomes with mitomycin C prodrug and ammonium-sulfate (x symbols), liposomes with co-encapsulated doxorubicin and mitomycin C prodrug, the doxorubicin loaded into the liposomes using an ammonium alendronate gradient (triangles), and liposomes with co-encapsulated doxorubicin and mitomycin C prodrug, the doxorubicin loaded into the liposomes using an ammonium sulfate gradient (diamonds)

As mentioned in Example 1, liposomes with co-encapsulated doxorubicin and mitomycin C prodrug were prepared by loading doxorubicin into the liposomes against an ammonium sulfate ion gradient or against an ammonium alendronate ion gradient. A study was done to evaluate the effect, if any, on in vitro cytotoxicity of liposomes with co-encapsulated doxorubicin and mitomycin C prodrug prepared with the two loading salts. The study was conducted using T24 bladder cancer carcinoma cells, and the results are shown in FIGS. 9A-9B. FIG. 9A shows the growth of T24 bladder cancer carcinoma cells as a percentage of control cells (untreated), as a function of doxorubicin concentration after incubation for 72 hours at 37° C. with free doxorubicin (circles), liposomes with entrapped doxorubicin (liposome-dox, DOXIL, squares), liposomes with co-encapsulated doxorubicin and mitomycin C prodrug, the doxorubicin loaded into the liposomes using an ammonium alendronate gradient (triangles), and liposomes with co-encapsulated doxorubicin and mitomycin C prodrug, the doxorubicin loaded into the liposomes using an ammonium sulfate gradient (diamonds). The cytotoxicity of the liposomes with co-encapsulated doxorubicin and mitomycin C prodrug was the same irrespective of the loading salt.

A similar result is seen in FIG. 9B when the cell growth as a function of mitomycin C (MMC) concentration was evaluated. T24 bladder cancer carcinoma cells treated with liposomes with co-encapsulated doxorubicin and mitomycin C prodrug, the doxorubicin loaded into the liposomes using an ammonium alendronate gradient (triangles), and with liposomes with co-encapsulated doxorubicin and mitomycin C prodrug, the doxorubicin loaded into the liposomes using an ammonium sulfate gradient (diamonds) had nearly identical cytotoxicity profiles. The cytotoxicity of the liposomes with co-encapsulated doxorubicin and mitomycin C prodrug was the same irrespective of the loading salt. Also shown in FIG. 9B are the results for cells treated with free mitomycin C (circles), liposomes with mitomycin C prodrug and ammonium-alendronate (squares), and liposomes with mitomycin C prodrug and ammonium-sulfate (x symbols). Similar to the result observed for liposomes with co-encapsulated doxorubicin and mitomycin C prodrug yielding the same cytotoxicity irrespective of loading salt, liposomes with mitomycin C prodrug and either ammonium alendronate salt or ammonium sulfate salt achieved similar cytotoxicity levels.

Considering the drug uptake study (FIGS. 3A-3B), where drug uptake was similar for all liposomal formulations, the in vitro cytotoxicity studies showing an enhanced cellular toxicity for cells treated with liposomes with co-encapsulated doxorubicin and mitomycin C prodrug (FIGS. 4-9) is not explained by a higher uptake of doxorubicin or mitomycin C prodrug. Instead, the combined presence of doxorubicin and mitomycin C prodrug when administered from a liposome delivery vehicle where the two agents are co-encapsulated provides a synergistic result.

The literature has reported that liposomes with a mitomycin C prodrug conjugate yield, within a 1-hour incubation period with a reducing agent such as dithiothreitol, mitomycin C prodrug conjugate in nearly stoichiometric amounts with the reducing agent (dithiothreitol). That is a dithiothreitol: mitomycin C prodrug conjugate molar ratio of ~1:1 is provided, leading to essentially complete degradation of mitomycin C prodrug conjugate. Dithiothreitol concentration of 0.5 mM is required for >99% cleavage of mitomycin C prodrug conjugate within the time lapse of 30 to 60 min that allows for completion of the reaction. Thus, the reaction is nearly stoichiometric since this concentration of dithiothreitol is just above the molar concentration of mitomycin C prodrug conjugate (0.44 mM) present in the reaction. Since the concentration of mitomycin C prodrug conjugate in liposomes with co-encapsulated doxorubicin and mitomycin C prodrug is lower by ~2-fold compared to liposomes with the mitomycin C prodrug conjugate, the equivalent concentration of dithiothreitol that should cause near-total cleavage of liposomes with co-encapsulated doxorubicin and mitomycin C prodrug is 0.25 mM. A study was done, as described in Example 4, to explore this concept.

Figure 10A:
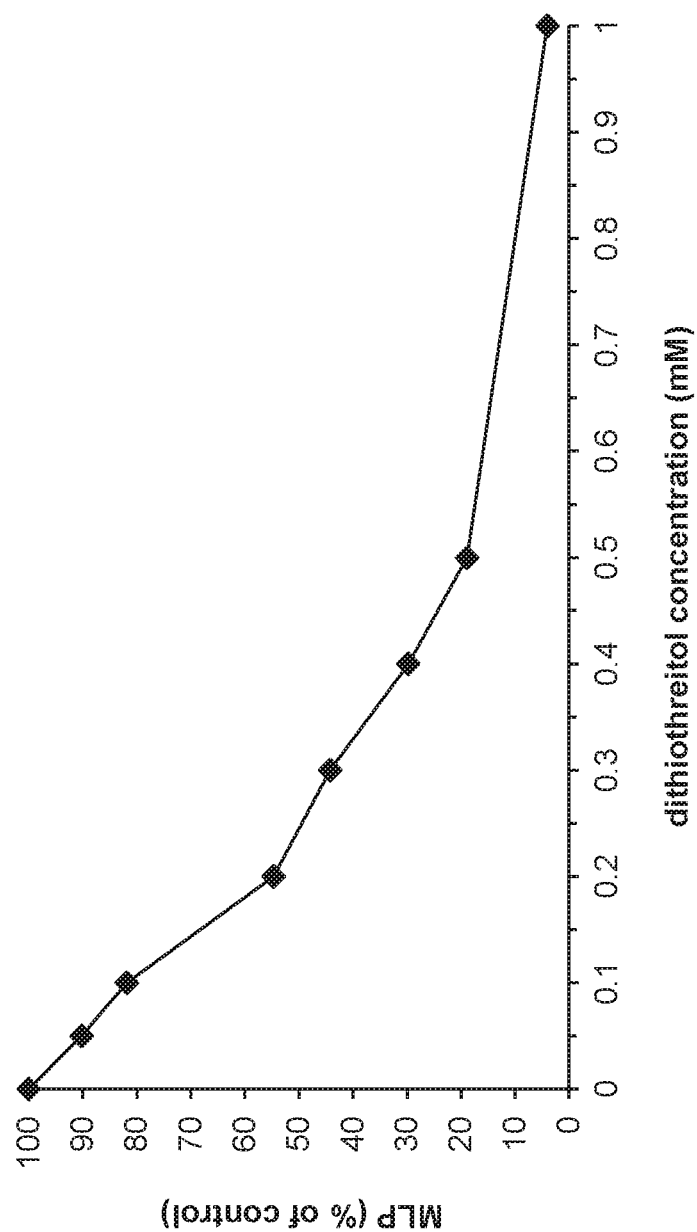
FIGS. 10A-10B are graphs showing cleavage of mitomycin C prodrug conjugate (FIG. 10A) and release of mitomycin C (FIG. 10B) as a percent of control, as a function of dithiothreitol (DTT) concentration, in mM, when liposomes with co-encapsulated doxorubicin and mitomycin C prodrug were incubated with DTT at 37° C. for 1 hour.
Figure 10B:
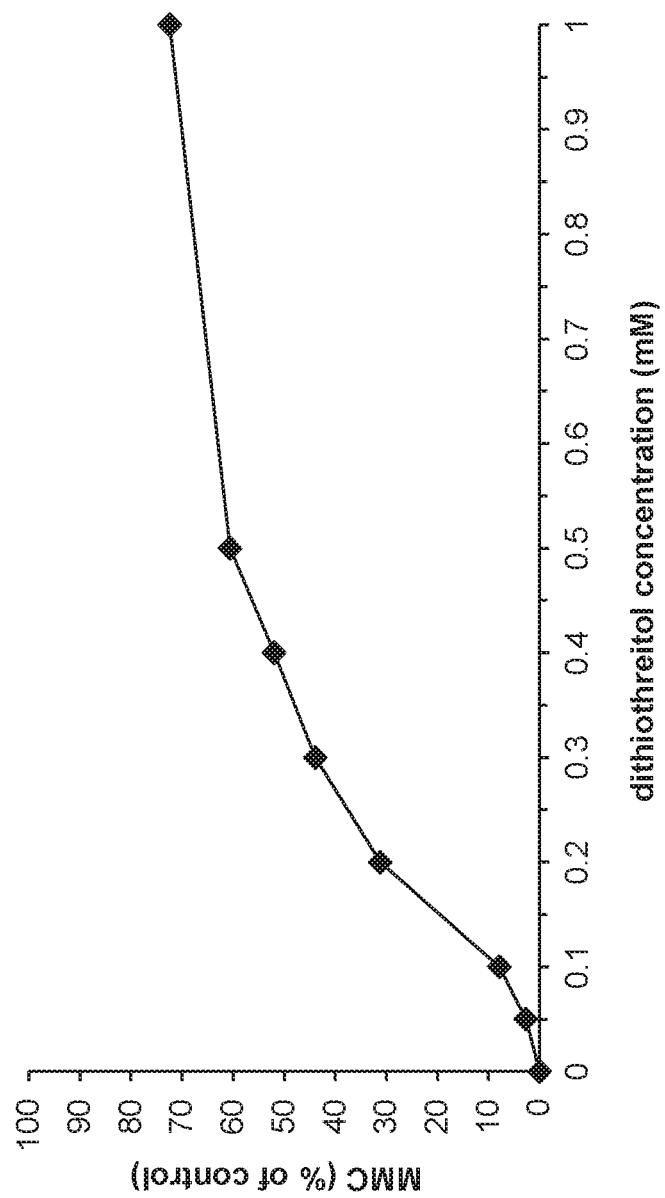
Figure 10C:
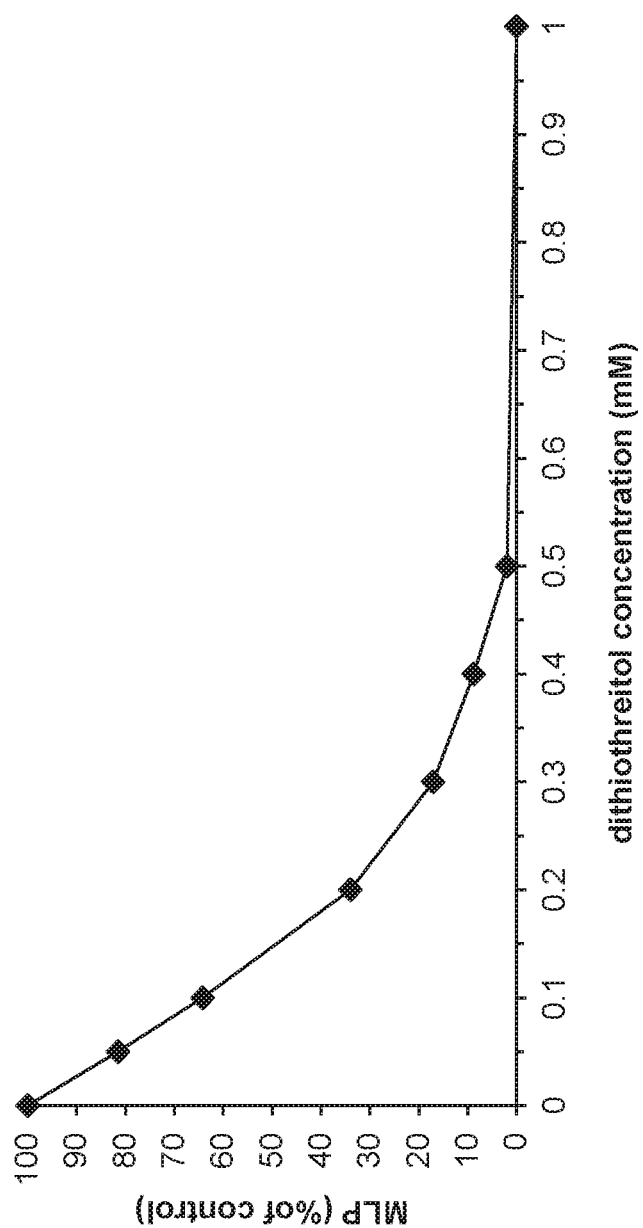
FIGS. 10C-10D are graphs showing cleavage of mitomycin C prodrug conjugate (FIG. 10C) and release of mitomycin C (FIG. 10D) as a percent of control, as a function of dithiothreitol (DTT) concentration, in mM, when liposomes with entrapped mitomycin C prodrug were incubated with DTT at 37° C. for 1 hour.
Figure 10D:
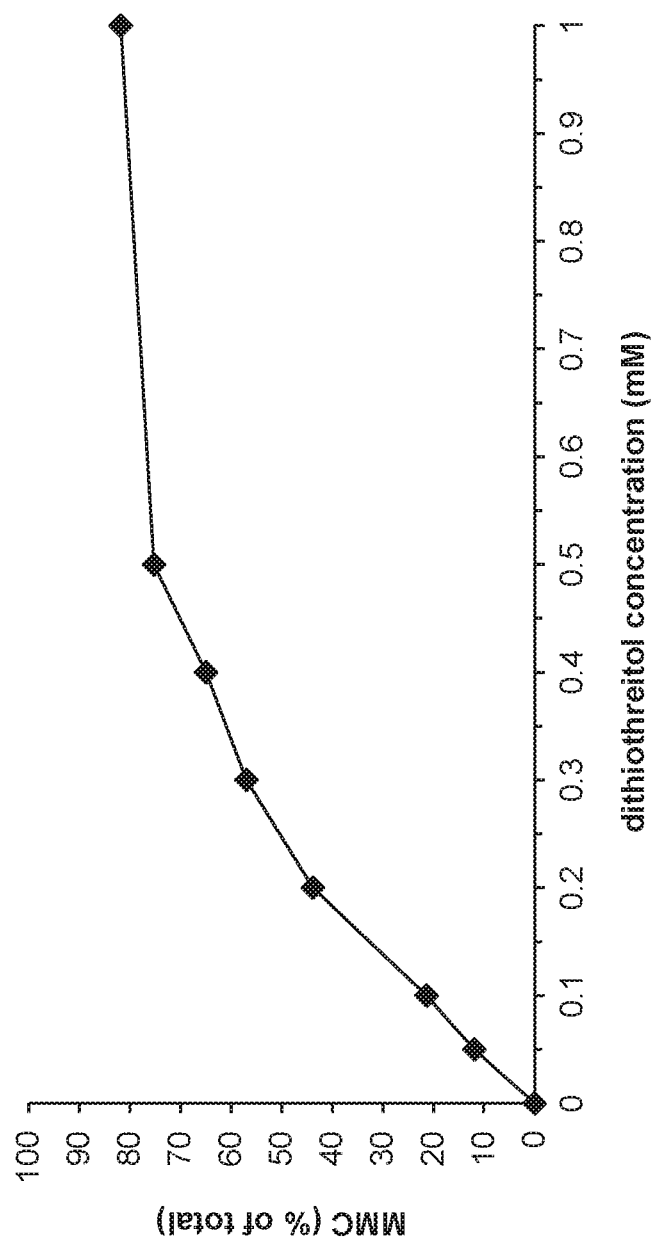

Results of the drug release assay from liposomes with co-encapsulated doxorubicin and mitomycin C prodrug are shown in FIGS. 10A-10B, where the dithiothreitol concentration dependence of mitomycin C prodrug activation at 37° C., i.e. cleavage of mitomycin C-lipid prodrug conjugate, and release of free mitomycin C by dithiothreitol is shown. The data shows that when incubation is prolonged to 1 hour, a 1:1 molar ratio of mitomycin C prodrug conjugate:dithiothreitol was not able to completely cleave mitomycin C prodrug conjugate and release mitomycin C as it was predicted by a simple stoichiometric reaction, suggesting that the liposomes with co-encapsulated doxorubicin and mitomycin C prodrug are more resistant to thiolytic cleavage of mitomycin C prodrug conjugate by dithiothreitol as compared to liposomes with only the mitomycin C prodrug conjugate. These results were confirmed when higher concentrations of dithiothreitol were used for the mitomycin C prodrug cleavage. The data in FIGS. 10A-10B show that even at dithiothreitol concentrations of 0.5 mM and 1 mM, there is not complete cleavage of the mitomycin C prodrug conjugate, indicating that mitomycin C prodrug conjugate is more resistant to activation in liposomes with co-encapsulated doxorubicin and mitomycin C prodrug as compared to liposomes with the mitomycin C prodrug conjugate (FIGS. 10C-10D). This is evident from the log slope of the lines, where the log slope of release of mitomycin C prodrug conjugate up to 0.5 mM dithiothreitol was greater for liposomes with mitomycin C prodrug conjugate (log slope 4.5) than for liposomes with co-encapsulated doxorubicin and mitomycin C prodrug conjugate (log slope 3.9).

An in vivo study was conducted, as described in Example 5, to evaluate treatment of a neoplasm in subjects treated with liposomes with co-encapsulated doxorubicin and mitomycin C prodrug. Using a mouse tumor metastatic C26 model, the toxicity and the therapeutic effect of liposomes with co-encapsulated doxorubicin and mitomycin C prodrug were compared to free mitomycin C and to liposomes with the mitomycin C prodrug conjugate (MLP-liposomes, or PROMITIL) and to liposomes with co-encapsulated mitomycin C prodrug and doxorubicin. The test agents were administered intravenously at days 5 and 12 after tumor cell inoculation at the dosages detailed in Example 5.

Figure 11:
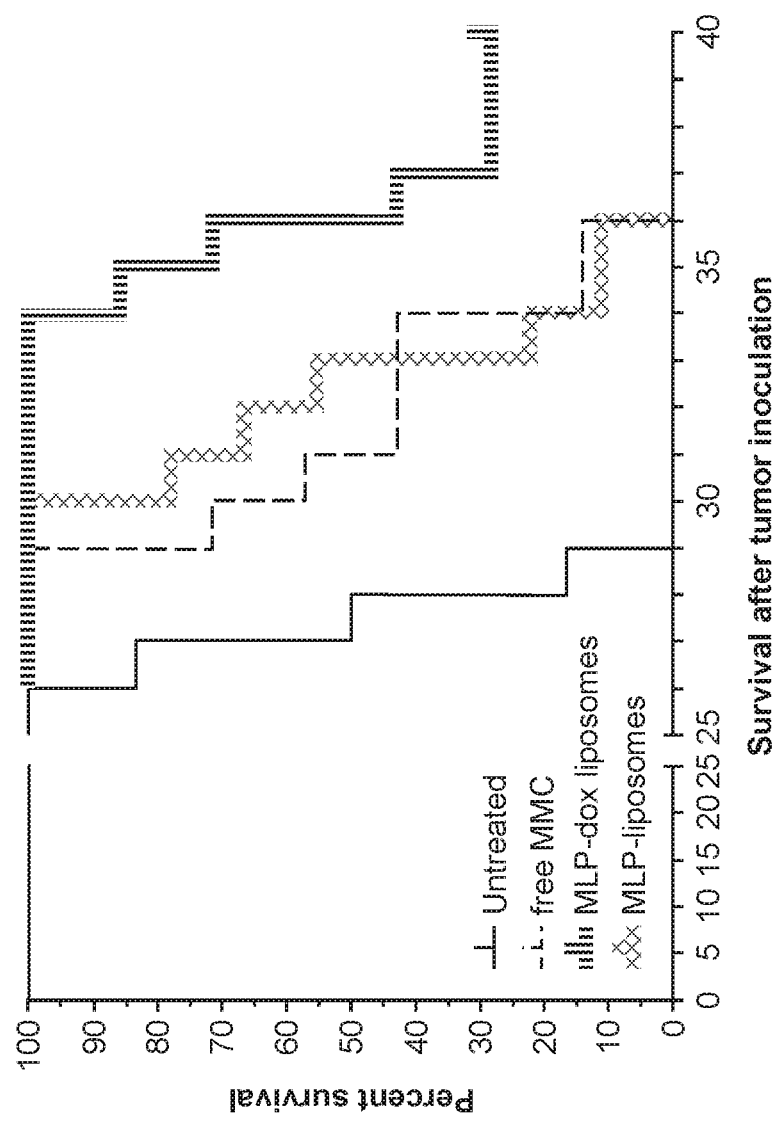
FIG. 11 is a graph of percent survival of mice bearing a C26 metastatic tumor and treated with free mitomycin C (free MMC, dashed line), liposomes with the mitomycin C prodrug conjugate (MLP-liposomes, x cross-hatched line), and liposomes with co-encapsulated doxorubicin and mitomycin C prodrug (liposome-MLP-dox, vertical stripe fill), or untreated (solid line)

Results are shown in FIG. 11 where percent survival of the tumor-bearing mice as a function of time is shown. Mice left untreated (solid line) had a median survival of 27.5 days. Mice treated with free mitomycin C (dashed line) had a median survival of 31 days. Mice treated with liposomes with the mitomycin C prodrug conjugate (cross-hatched line) had a median survival of 33 days. Mice treated with liposomes with co-encapsulated doxorubicin and mitomycin C prodrug (vertical stripe fill) had a median survival of 36 days. At day 36, there were no clear toxic effects due to treatment with liposomes with co-encapsulated doxorubicin and mitomycin C prodrug, with the exception of one mouse that was sacrificed at day 18, as compared with the other treatments. The therapeutic effect of liposomes with co-encapsulated doxorubicin and mitomycin C prodrug was superior to other treatment groups based on the survival time (see p values).

Figure 12:
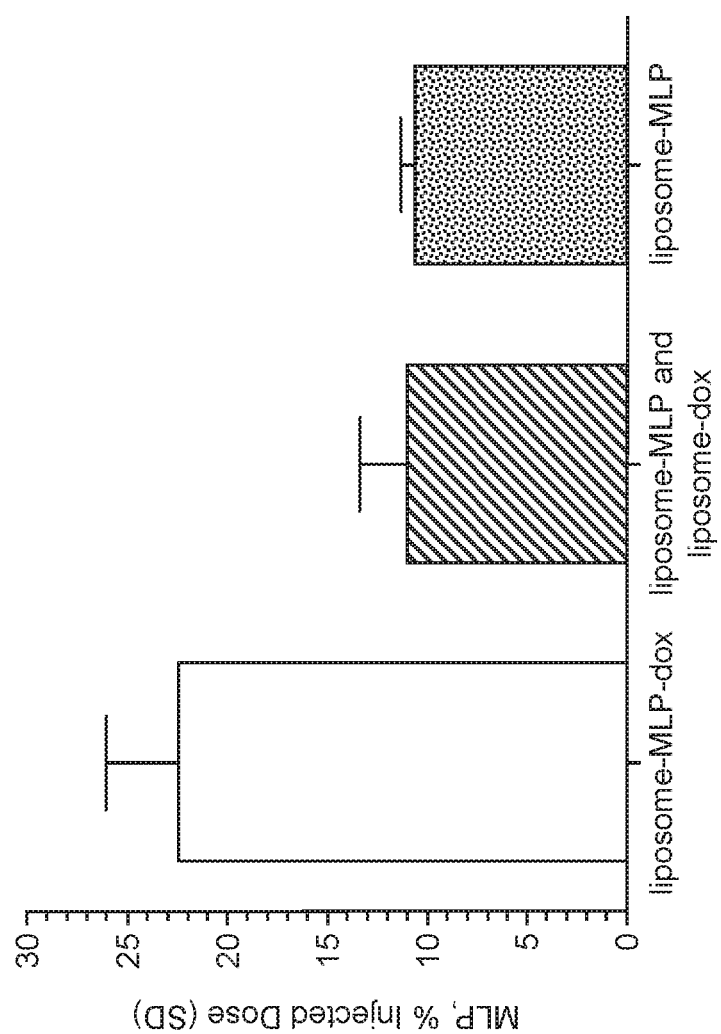
FIG. 12 is a bar graph showing the percent of mitomycin C prodrug conjugate (MLP) in the blood stream 24 hours after injection of (i) liposomes co-encapsulating doxorubicin and mitomycin C prodrug conjugate (liposome-MLP-dox), (ii) liposomes with the mitomycin C prodrug conjugate (liposome-MLP), or (iii) a combination of liposomes with entrapped doxorubicin (liposome-dox) and of liposomes with the mitomycin C prodrug conjugate (liposome-MLP)

Another in vivo study was conducted to determine the pharmacokinetic profile of the liposomes with co-encapsulated doxorubicin and mitomycin C prodrug. In this study, liposomes were prepared as described herein to co-encapsulate doxorubicin and mitomycin C prodrug conjugate. Animals were injected with liposomes co-encapsulating doxorubicin and mitomycin C prodrug conjugate, or with liposomes with the mitomycin C prodrug conjugate, or with a combination of liposomes with entrapped doxorubicin and of liposomes with the mitomycin C prodrug conjugate. Blood samples were taken 24 hours after injection and the amount of mitomycin C prodrug conjugate in the blood plasma relative to the dose injected was measured. Results are shown in FIG. 12. Liposomes with the mitomycin C prodrug conjugate (liposome-MLP, or PROMITIL) and a combination of liposomes with entrapped doxorubicin and of liposomes with the mitomycin C prodrug conjugate (liposome-MLP+liposome-dox) had about 11% mitomycin C prodrug conjugate (MLP) in the plasma 24 hours after injection. Liposomes with co-encapsulated doxorubicin and mitomycin C prodrug had about 22% mitomycin C prodrug conjugate (MLP) in the plasma 24 hours after injection. Thus, the amount of mitomycin C prodrug conjugate in the blood stream 24 hours after administration is about 2-fold higher when mitomycin C prodrug conjugate is administered co-encapsulated in liposomes with doxorubicin (or another anthracycline) than when liposomes with mitomycin C prodrug conjugate and liposomes with entrapped doxorubicin are co-administered, each drug in a separate liposomal vehicle. The initial ratio of mitomycin C prodrug conjugate to doxorubicin for animals treated with liposomes with co-encapsulated doxorubicin and mitomycin C prodrug was 1.26, and the plasma ratio of mitomycin C prodrug conjugate to doxorubicin was 0.83. However, the mitomycin C prodrug conjugate concentration was two-fold greater for treatment with liposomes with co-encapsulated doxorubicin and mitomycin C prodrug than that for treatment with liposomes with mitomycin C prodrug, with or without with liposomal doxorubicin.

Figures 13A, 13B:
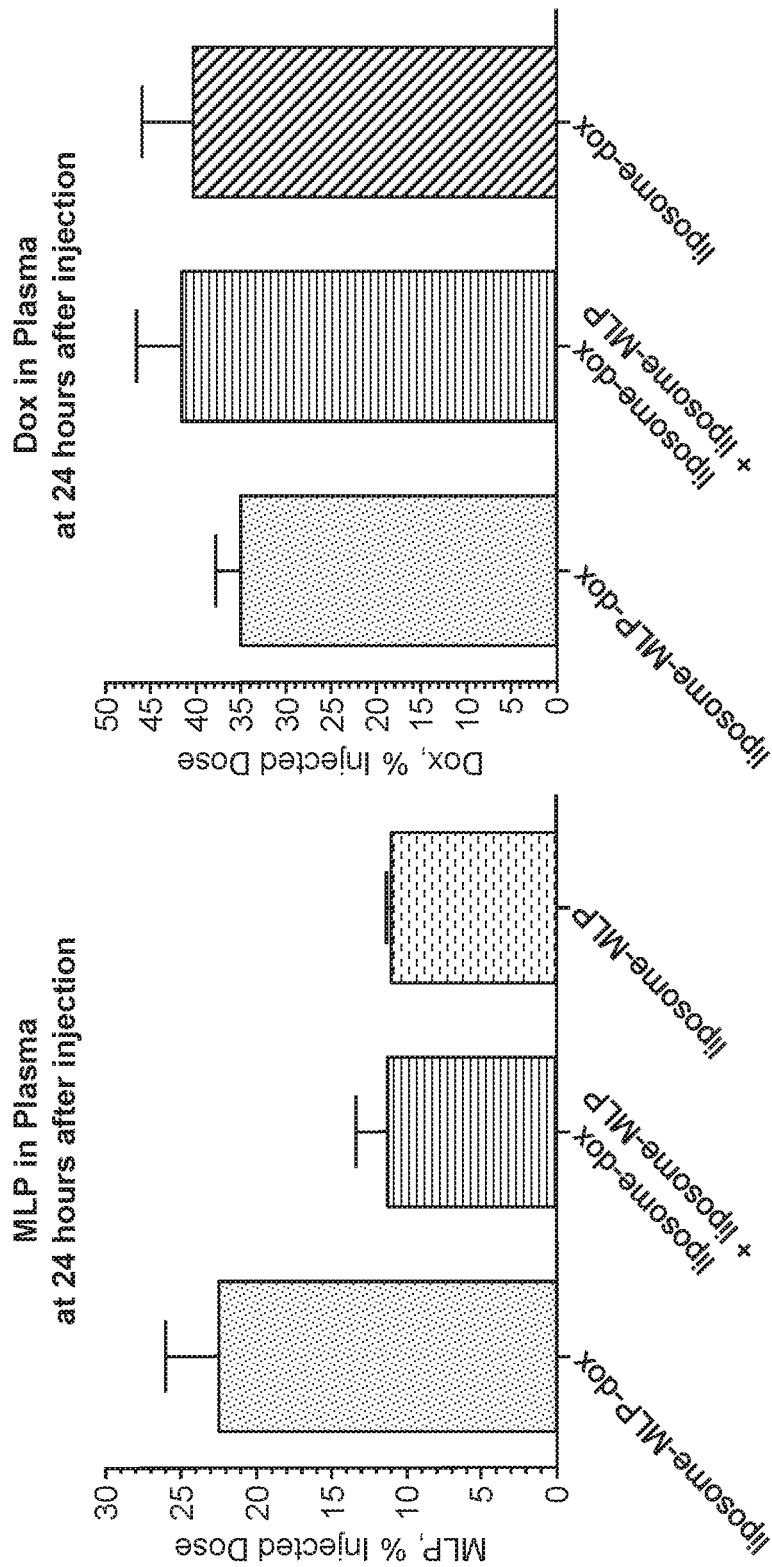
FIGS. 13A-13B are bar graphs showing the percent of injected dose of mitomycin C prodrug conjugate (MLP, FIG. 13A) and of doxorubicin (Dox, FIG. 13B) in plasma in mice 24 hours after injection of liposomes with co-encapsulated doxorubicin and mitomycin C prodrug (liposome-MLP-dox, dotted bars), of a mixture of liposomes with mitomycin C prodrug conjugate (liposome-MLP) and of liposomes with entrapped doxorubicin (liposome-dox) (bars with horizontal lines), or of liposomes with mitomycin C prodrug conjugate (liposome-MLP, FIG. 13A only, brick fill) or liposomes with doxorubicin (liposome-dox, FIG. 13B only, diamond fill)

Other in vivo studies were conducted to demonstrate the synergistic behavior of liposomes with co-encapsulated doxorubicin and mitomycin C prodrug. In one study, described in Example 6, the pharmacokinetics and tissue distribution of mitomycin C prodrug conjugate and of doxorubicin 24 hours after injection of liposomal formulations were determined. Animals were intravenously injected with the test formulations, and 24 hours later the concentration of mitomycin C prodrug conjugate (MLP) and of doxorubicin in the plasma was determined. The results are in FIGS. 13A-13B, where the percent of injected dose of mitomycin C prodrug conjugate is shown in FIG. 13A and the percent of injected dose of doxorubicin is shown in FIG. 13B. FIG. 13A shows that administration of liposomes with co-encapsulated doxorubicin and mitomycin C prodrug (liposome-MLP-dox, dotted bars) provides a nearly two-fold higher amount of mitomycin C prodrug conjugate in the plasma than that provided from administration of a mixture of liposomes with mitomycin C prodrug conjugate (liposome-MLP) and of liposomes with entrapped doxorubicin (liposome-dox) (bars with horizontal lines), or of liposomes with mitomycin C prodrug conjugate (liposome-MLP, bars with brick fill). This data evidences the longer blood circulation time of the liposome-MLP-dox formulation and its stability of the MLP conjugate when part of the liposome-MLP-dox formulation. FIG. 13B shows that the plasma pharmacokinetics of doxorubicin was not significantly different when doxorubicin is provided in the form of liposome-MLP-dox (dotted bars), a mixture of liposome-MLP and liposome-dox (bars with horizontal lines) or liposomes with doxorubicin (liposome-dox, diamond filled bars). Accordingly, in one embodiment, the liposomal formulation with co-encapsulated doxorubicin and mitomycin C prodrug conjugate described herein provides, relative to liposome entrapped mitomycin C prodrug conjugate, administered as a single treatment agent or co-administered with liposome entrapped doxorubicin, a blood circulation lifetime that is 10%, 15%, 20%, 25%, or 30% longer.

The distribution of mitomycin C prodrug conjugate (MLP) and of doxorubicin in the mice treated with liposome-MLP-dox were determined. Also, the distribution of MLP in the mice treated with liposome-MLP was determined. FIG. 14A shows the percent of injected dose per gram of tissue of MLP (open bars) and of doxorubicin (dotted bars) 24 hours after injection of liposomes with co-encapsulated doxorubicin and mitomycin C prodrug (liposome-MLP-dox). MLP and doxorubicin were present in mice liver, spleen, lung, and kidney, with about 1% of the injected dose of MLP detectable in each of these tissues when MLP is administered in the co-encapsulated MLP-doxorubicin liposome formulation (FIG. 14A). In contrast, when MLP is administered in the form of liposome-entrapped mitomycin C prodrug conjugate, no MLP is detected in the liver or lung (FIG. 14B). This data indicates that MLP administered in the form of liposomes that co-encapsulate doxorubicin and mitomycin C prodrug conjugate has a slower rate of degradation and/or cleavage relative to MLP administered in the form of liposome-entrapped MLP. In one embodiment, the liposomal formulation with co-encapsulated doxorubicin and mitomycin C prodrug conjugate provides, relative to liposome entrapped mitomycin C prodrug conjugate, a 10%, 15%, 20%, 25%, or 30% higher amount of MLP in the liver, the lung and/or the spleen.

Figure 15:
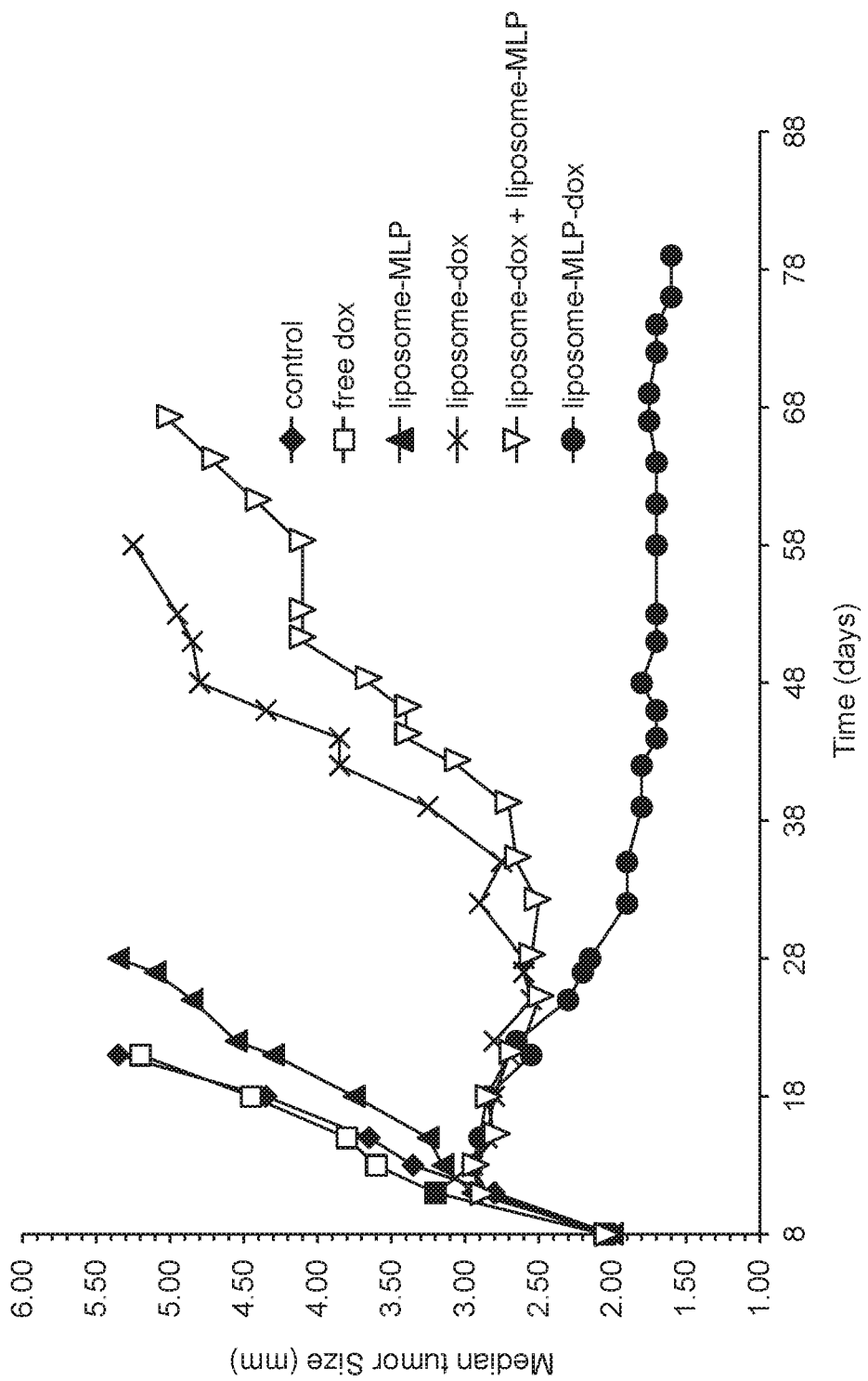
FIG. 15 is a graph showing median tumor size, in mm, of a 4T1 breast tumor in mice, as a function of time, in days, in untreated (control) tumor-bearing mice (closed diamonds) and in tumor-bearing mice treated with (i) free doxorubicin (open squares), (ii) liposomes with mitomycin C prodrug conjugate (liposome-MLP, closed triangles), (iii) liposomes with entrapped doxorubicin (liposome-dox, x symbols), (iv) a mixture of liposomes with mitomycin C prodrug conjugate (liposome-MLP) and of liposomes with entrapped doxorubicin (liposome-dox) (inverted open triangles), or (v) liposomes with co-encapsulated doxorubicin and mitomycin C prodrug (closed circles).

Another in vivo study was conducted using mice bearing 4T1 breast tumors to evaluate the antitumor activity of liposomes with co-encapsulated doxorubicin and mitomycin C prodrug. As described in Example 7, tumor-bearing mice were treated free doxorubicin or with a liposome formulation. Tumor size was measured every two days for about 70 days after treatment. Results are shown in FIG. 15, where untreated tumor-bearing mice are designated by closed diamonds and the drug treated, tumor-bearing mice treated with the liposomal formulations were as follows: (i) free doxorubicin (open squares), (ii) liposomes with mitomycin C prodrug conjugate (liposome-MLP, closed triangles), (iii) liposomes with entrapped doxorubicin (liposome-dox, x symbols), (iv) a mixture of liposomes with mitomycin C prodrug conjugate (liposome-MLP) and of liposomes with entrapped doxorubicin (liposome-dox) (inverted open triangles), or (v) liposomes with co-encapsulated doxorubicin and mitomycin C prodrug (closed circles).

With reference to FIG. 15, tumor-bearing mice left untreated (closed diamonds) and those treated with free doxorubicin (open squares) experienced continued and rapid tumor growth with the tumor approaching 5.5 mm 10 days after treatment. The tumor-bearing mice treated with liposome-MLP (closed triangles) experienced continued tumor growth with the tumor approaching 5.5 mm about 20 days after treatment. In the group of tumor-bearing mice treated with liposome-dox (x symbols), tumor growth was slowed relative to mice treated with free doxorubicin or left untreated, and 1/8 animals remained tumor free. In the group of tumor-bearing mice treated with a mixture of liposome-MLP and liposome-dox (inverted open triangles), tumor growth was slowed relative to mice treated with free doxorubicin, liposome-dox, liposome-MLP, or left untreated, and 2/8 animals remained tumor free. In the group of tumor-bearing mice treated with liposome-MLP-dox (liposomes with co-encapsulated doxorubicin and mitomycin C prodrug, closed circles), the tumor growth was reversed and 4/8 of the animals were tumor free.

The data from this in vivo study demonstrates the potency of the liposomes with co-encapsulated doxorubicin and mitomycin C prodrug conjugate that arises by the synergistic activity of the formulation. Notably, the increased potency of the co-encapsulated doxorubicin and mitomycin C prodrug conjugate, as evidenced by the reduction of tumor size and number of tumor-free subjects, relative to the other test formulations was achieved with a lower dose of mitomycin C prodrug conjugate than given in the liposome entrapped mitomycin C prodrug conjugate (liposome-MLP or PROM-ITIL). Accordingly, the liposomal formulation with co-encapsulated doxorubicin and mitomycin C prodrug conjugate described herein provides, in one embodiment, a 10%, 20%, 25% or 30% increase in potency, relative to liposome entrapped mitomycin C prodrug conjugate, administered as a single treatment agent or co-administered with liposome entrapped doxorubicin, at a dose of mitomycin C prodrug conjugate that is 30%, 25%, 20% or 15% lower than the dose given in the liposome entrapped mitomycin C prodrug conjugate composition.

Treatment Modalities and Patient Populations

As can be appreciated based on the studies described above, a method of treatment based on a liposome composition comprised of liposomes with co-encapsulated doxorubicin and mitomycin C prodrug provides for the synergistic treatment of a neoplasia in a subject in need of treatment. Neoplasias for which the treatment methods are particularly useful include, without limitation, carcinomas, particularly those of the bladder, breast, cervix, colon, head and neck, melanoma, lung, ovary, pancreas, esophagus, anal, and stomach. In a preferred embodiment, a method is provided for the synergistic treatment of breast, colon or colorectal, stomach, esophageal and pancreatic cancers. Advantageously, the synergistic method achieves beneficial effects including reducing the growth of tumors, reducing tumor burden, and/or producing tumor regression in a mammalian host. The method also prolongs survival of a tumor-bearing mammal.

One skilled in the art appreciates that a pharmaceutical composition comprising a population of liposomes with co-encapsulated doxorubicin and mitomycin C prodrug can be administered to a subject by various routes including, for example, injection directly into a tumor, orally or parenterally, such as intravenously, intramuscularly, subcutaneously, intraorbitally, intranasally, intracapsularly, intraperitoneally, intracisternally, intra-tracheally, or intra-articularly. In a particular embodiment, the composition is administered parenterally as a solution in normal saline.

The actual dosage of the liposomal composition may be varied depending upon the requirements of the patient and the severity of the condition being treated. Determination of the proper dosage for a particular situation is within the skill of the art. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

III. Examples

The following examples are illustrative in nature and are in no way intended to be limiting.

EXAMPLE 1

Liposome Preparation

A prodrug conjugate of mitomycin C releasably attached to a lipophilic moiety, para-diacyldiglyceroldithiobenzyl-mitomycin C, was synthesized as described in U.S. Pat. No. 7,303,760, in Example 2, incorporated by reference herein.

Liposome formation was performed by standard methods using ethanol injection, hydration and polycarbonate membrane extrusion down to 0.08 μm pore size. Specifically, liposomes with an external coating of polyethylene glycol and the mitomycin C prodrug conjugate were prepared using hydrogenated soy phosphatidylcholine (HSPC), mPEG$_{2000}$-DSPE (methoxy-polyethylene glycol (MW 2,000 Daltons) attached to disteroylphosphatidylethanolamine), cholesterol and the mitomycin C prodrug conjugate at a percent molar ratio of 55:5:30:10, respectively. An ammonium salt of alendronate was encapsulated into the liposomes by rehydration in buffer containing 250 mM ammonium alendronate at pH 6.7. Non-encapsulated alendronate ammonium salt was removed by dialysis followed by passage over DOWEX® anion exchange resin. SEPHAROSE® column chromatography was conducted to inspect for free alendronate.

The liposomes containing alendronate in the water phase and mitomycin C prodrug in the lipid bilayer were incubated with a solution of doxorubicin hydrochloride (dox) for 60 minutes at 60° C. The resulting liposome suspension was passed through DOWEX cation exchange resin to remove any non-encapsulated doxorubicin. The formulation was sterilized using 0.45 μm and 0.22 μm filters. To determine whether there was any residual free doxorubicin and to follow encapsulation stability, SEPHAROSE gel chromatography fractionation was used to separate liposomal material from non-encapsulated, low molecular weight material. Phospholipid and alendronate content were determined after Folch extraction. Doxorubicin absorbance was measured by fluorescence emission at 590 nm (Ex: 470 nm) following acidified isopropanol extraction, and mitomycin C prodrug by reverse phase HPLC with UV detection at 360 nm following isopropanol extraction.

A similar liposome composition was prepared except doxorubicin was loaded into the liposomes using an ammonium sulfate ion gradient of 250 mM ammonium sulfate at pH 5.8, instead of an ammonium alendronate gradient.

The final formulation of the liposome compositions are shown in the table below.

| | Ammonium alendronate loaded | Ammonium sulfate loaded |
|---|---|---|
| Final Vol. | 26.5 mL | 18 mL |
| pH | 6.8 | 7.0 |
| Osm | 289 mOsm/L | 305 mOsm/L |
| Size | 119 nm diam. polydispersity index 0.057 | 129 nm diam polydispersity index 0.049 |
| PL (Phospholipid) | 10.05 μmol/mL | 30.63 μmol/mL |
| mitomycin C prodrug (MLP) | 2.10 μmol/mL, 2.44 mg/mL | 2.72 μmol/mL, 3.1 mg/mL |
| alendronate | 2.65 μmol/mL, 0.86 mg/mL | NA |
| doxorubicin | 3.26 μmol/mL, 1.89 mg/mL | 4.8 μmol/mL, 2.8 mg/mL |
| doxorubicin/mitomycin C prodrug molar ratio | .55 | 1.75 |

EXAMPLE 2

Liposome Characterization

Liposomes prepared according to Example 1 were inspected by electron cryomicroscopy (cryoTEM). Images are shown in FIGS. 1A-1D.

Plasma stability of liposomes prepared according to Example 1 was assessed by incubation of 100 μL of the liposomes with 400 μL of human plasma at 37° C. for 2 hours. After incubation, the liposomes were assessed for release of MLP and DOX by passing a sample of the liposomes through a column of Sepharose-6G and 20 mL eluent was collected. Results are shown in FIGS. 2A-2B.

EXAMPLE 3

In Vitro Characterization: Cell Uptake and Cytotoxicity

The cytotoxicity of liposomes with co-encapsulated doxorubicin and mitomycin C prodrug conjugate were evaluated in three human cell lines: T24 bladder carcinoma, N87 gastric carcinoma and IGROV-1 ovarian carcinoma cells and in the multidrug resistant M109R lung carcinoma cell line and NCI/ADR ovarian carcinoma cells. For comparison, liposomes with entrapped doxorubicin with ammonium sulfate gradient and a coating of polyethyleneglycol (PEG) (available under the tradename DOXIL®), liposomes with the mitomycin C prodrug conjugate incorporated into the lipid bilayer and a coating of PEG (sometimes referred to in the literature by the tradename PROMITIL®) were also evaluated in the cell lines, along with free doxorubicin and liposomes with encapsulated doxorubicin with ammonium alendronate gradient and a coating of PEG (U.S. 2014/0328899, incorporated by reference herein).

Cell uptake studies were done as follows. $1\times10^6$ cells were incubated for 3 hours with the various test agents at a doxorubicin concentration of 6.5 µmoles/mL (3.7 µg/mL) and final mitomycin C lipid prodrug conjugate concentration of 5 µmoles/mL (5.7 µg/mL) and a phospholipid concentration similar to that of liposomes with entrapped doxorubicin (40 nanomoles/mL). Results are shown in FIG. 3A-3B and in Table 1.

In the cytotoxicity assay, cells were seeded in 96-multi-well plates. After overnight incubation, the drugs or liposome compositions were added at various concentrations and cells were incubated further for a total exposure of 72 hrs. Cell growth was evaluated colorimetrically with methylene blue staining and growth rates and $IC_{50}$ values were calculated as known in the literature. Results are shown in FIGS. 4-9 and Tables 2-6.

EXAMPLE 4

Drug Release Assay

An assay to measure the release of mitomycin C from the mitomycin C prodrug conjugate incorporated into the liposomes with co-encapsulated doxorubicin and mitomycin C prodrug was conducted by incubating the liposomes with dithiothreitol (DTT).

In the studies, liposomes with 250 µg of mitomycin C prodrug (PROMITIL, 50 µL) or with co-encapsulated doxorubicin and mitomycin C prodrug conjugate were incubated in a final volume of 0.5 mL PBS with various concentrations of dithiothreitol at 37° C. for 1 hour with shaking. The reaction was stopped by dilution and drug extraction was done with isopropanol (1:10). Mitomycin C prodrug conjugate and free mitomycin C were quantified by HPLC analysis. Results are shown in FIGS. 10A-10D.

EXAMPLE 5

In Vivo Study: Therapeutic Effect of Liposomes with Co-Encapsulated Doxorubicin and Mitomycin C Prodrug An in vivo study was carried out in a mouse tumor metastatic C26 model to test the toxicity and the therapeutic effect of liposomes with co-encapsulated doxorubicin and mitomycin C prodrug (prepared according to Example 1) compared to free mitomycin C and to liposomes with the mitomycin C prodrug conjugate (liposome-MLP or PROMITIL). In this study, 50,000 C26 mouse colon carcinoma cells were inoculated intravenously into syngeneic BALB/c recipients in order to produce metastatic tumors. The test agents were administered intravenously at days 5 and 12 after cell inoculation. The dose per treatment was 5 mg/kg for free mitomycin C, 30 mg/kg mitomycin C prodrug conjugate (MLP) for liposomes with the mitomycin C prodrug conjugate (PROMITIL), and 12.5 mg/kg mitomycin C prodrug conjugate (MLP) with 8 mg/kg doxorubicin for liposomes with co-encapsulated mitomycin C prodrug conjugate and doxorubicin. Results are shown in FIG. 11.

EXAMPLE 6

In Vivo Study: Pharmacokinetics of Mitomycin C Prodrug and of Doxorubicin 24 Hours after Administration of Liposomes with Co-Encapsulated of the Two Agents Balb/c inbred and Sabra outbred mice were randomized into four groups (n=*) for treatment with one of the following liposomal formulations: (i) liposomes with co-encapsulated doxorubicin and mitomycin C prodrug (prepared according to Example 1; liposome-MLP-dox); (ii) a mixture of liposomes with mitomycin C prodrug conjugate (liposome-MLP) and of liposomes with entrapped doxorubicin (liposome-dox); (iii) liposomes with mitomycin C prodrug conjugate (liposome-MLP); or (iv) liposomes with doxorubicin (liposome-dox).

The liposomal formulations were administered intravenously at the following doses:
(i) liposome-MLP-dox: 11 mg/kg mitomycin C prodrug conjugate (MLP) and 8 mg/kg doxorubicin;
(ii) mixture of liposome-MLP+liposome-dox: 30 mg/kg mitomycin C prodrug conjugate (MLP) and 5 mg/kg doxorubicin
(iii) liposome-MLP: 30 mg/kg mitomycin C prodrug conjugate (MLP); and
(iv) liposome-dox: 8 mg/kg doxorubicin.
24 hours after administration, the percent of injected dose of drug in the plasma was determined. Results are shown in FIGS. 13A-13B.

The distribution of mitomycin C prodrug conjugate (MLP) and of doxorubicin (dox) in the liver, spleen, lung and kidney of mice treated with formulation (i), liposome-MLP-dox, was determined, and is shown in FIG. 14A. The distribution of mitomycin C prodrug conjugate (MLP) in the liver, lung, spleen, kidney, and heart of mice treated with formulation (iii), liposome-MLP, was determined, and is shown in FIG. 14B.

EXAMPLE 7

In Vivo Study: Antitumor Activity of Liposomes with Co-Encapsulated Mitomycin C Prodrug and Doxorubicin An in vivo study was carried out in a mouse 4T1 breast tumor model to evaluate the toxicity and the therapeutic effect of liposomes with co-encapsulated doxorubicin and mitomycin C prodrug (prepared according to Example 1) compared to untreated, tumor-bearing mice and to tumor-bearing mice treated with free doxorubicin or with comparative liposomal formulations. BALB/c mice were inoculated intravenously with 100,000 cells 4T1 breast cancer cells to produce tumors. Three were approximately eight tumor-bearing mice in each of the treatment groups.

Eight days after inoculation, the test formulations were administered intravenously. The test formulations and doses were:
(i) free doxorubicin: 10 mg/kg;
(ii) liposome-MLP: 35 mg/kg mitomycin C prodrug conjugate (MLP);
(iii) mixture of liposome-MLP+liposome-dox: 17 mg/kg mitomycin C prodrug conjugate (MLP) and 10 mg/kg doxorubicin;

(iv) liposome-dox: 10 mg/kg doxorubicin; and
(v) liposomes with co-encapsulated doxorubicin and mitomycin C prodrug (liposome-MLP-dox): 12.5 mg/kg mitomycin C prodrug conjugate (MLP) and 10 mg/kg doxorubicin Tumor size was measured every two days after administration of the test formulations. Results are shown in FIG. 15.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A composition, comprising:
liposomes comprising a lipid layer defining an internal aqueous compartment, doxorubicin entrapped in the internal aqueous compartment and a mitomycin C prodrug incorporated into the lipid layer; and
a pharmaceutically acceptable carrier;
wherein the mitomycin C prodrug is a conjugate of mitomycin C releasably attached to a lipophilic moiety, and is of the form:

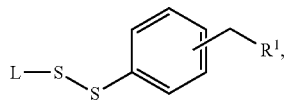

wherein L is a hydrophobic moiety, $R^1$ represents a mitomycin C residue, the —$CH^2R^1$ group is selected from the ortho position and the para position, wherein the liposomes comprise hydrogenated soy phosphatidylcholine (HSPC), mPEG2000-DSPE (methoxy-polyethylene glycol (MW 2,000 Daltons) attached to disteroylphosphatidylethanolamine), and cholesterol.

2. The composition of claim 1, wherein the prodrug is a conjugate of mitomycin C releasably attached to a lipophilic moiety.

3. The composition of claim 2, wherein the lipophilic moiety is a phospholipid.

4. The composition of claim 1, wherein the lipid layer is a lipid bilayer.

5. The composition of claim 1, further comprising an ammonium salt.

6. The composition of claim 5, wherein the ammonium salt is an ammonium salt of a bisphosphonate.

7. The composition of claim 6, wherein the bisphosphonate is selected from alendronate, pamidronate, neridonate, olpadronate, ibandronate, risedronate and zoledronate.

8. The composition of claim 5, wherein the ammonium salt is an ammonium salt of sulfate, phosphate, glucuronide, sucralfate, or dextran-sulfate.

9. The composition of claim 1, further comprising an ammonium salt of sulfate or alendronate.

10. A method for treating a neoplasm in a patient, comprising:
providing a composition comprised of liposomes comprising a lipid layer defining an internal aqueous compartment, doxorubicin entrapped in the internal aqueous compartment and a mitomycin C prodrug incorporated into the lipid layer, and a pharmaceutically acceptable carrier; and
administering or instructing to administer the composition;
wherein the mitomycin C prodrug is a conjugate of mitomycin C releasably attached to a lipophilic moiety, and is of the form:

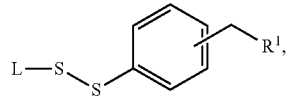

wherein L is a hydrophobic moiety, $R^1$ represents a mitomycin C residue, the —$CH^2R^1$ group is selected from the ortho position and the para position,
wherein the liposomes comprise hydrogenated soy phosphatidylcholine (HSPC), mPEG2000-DSPE (methoxy-polyethylene glycol (MW 2,000 Daltons) attached to disteroylphosphatidylethanol-amine), and cholesterol,
wherein the neoplasma in the patient is bladder cancer, gastric cancer, ovarian cancer, lung cancer, colon cancer, and breast cancer.

11. The method of claim 10, wherein said administering or instructing to administer comprises administering or instructing to administer via injecting.

12. The method of claim 11, wherein said injecting is by intravenous, intraarterial, intraperitoneal, intrapleural, intrathecal, intravesical or intratumoral injection.

13. The method of claim 10, wherein providing comprises providing an amount of the composition to yield a therapeutically-effective amount of mitomycin C in vivo.

* * * * *